United States Patent [19]

Clemence et al.

[11] Patent Number: 5,324,839

[45] Date of Patent: Jun. 28, 1994

[54] NITROGENOUS BICYCLIC DERIVATIVES SUBSTITUTED WITH BENZYL

[75] Inventors: Francois Clemence; Michel Fortin, both of Paris; Jean-Luc Haesslein, Courtry, all of France

[73] Assignee: Roussel-Uclaf, France

[21] Appl. No.: 832,003

[22] Filed: Feb. 6, 1992

[30] Foreign Application Priority Data

Feb. 7, 1991 [FR] France ................................ 91 01373
Aug. 20, 1991 [FR] France ................................ 91 10434

[51] Int. Cl.$^5$ .................. C07D 215/14; C07D 403/02; C07D 401/10; A61K 31/47; A61K 31/41; A61K 31/42; A61K 31/425
[52] U.S. Cl. .................................... 546/174; 546/146; 546/147; 546/148; 546/175; 546/176; 514/311
[58] Field of Search ............... 546/174, 175, 176, 146, 546/147, 148; 514/311, 314, 307

Primary Examiner—David B. Springer
Attorney, Agent, or Firm—Bierman and Muserlian

[57] ABSTRACT

Novel bicyclic compounds in all possible racemic, enantiomeric and diasteroisomeric forms of the formula

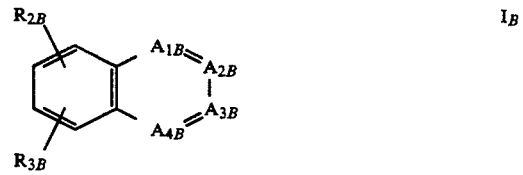

having antagonistic properties for angiotensin II receptors and novel intermediates and process for their preparation.

4 Claims, No Drawings

NITROGENOUS BICYCLIC DERIVATIVES SUBSTITUTED WITH BENZYL

OBJECTS OF THE INVENTION

It is an object of the invention to provide the novel compounds of formula I and their non-toxic, pharmaceutically acceptable salts and a novel process and intermediates for their preparation.

It is another object of the invention to provide novel compositions and a method for inhibiting the effects of angiotensin II.

These and other objects and advantages of the invention will become obvious from the following detailed description.

THE INVENTION

The novel compounds of the invention are selected from the group consisting of all possible racemic, enantiomeric and diastereoisomeric isomeric isomer forms of a compound of the formula

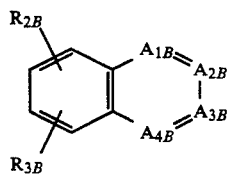

I$_B$ wherein R$_{2B}$ and R$_{3B}$ are individually selected from the group consisting of a) hydrogen, halogen, hydroxyl, mercapto, cyano, nitro, sulfo, formyl, benzoyl, acyl and acyloxy of up to 12 carbon atoms, free, salified and esterified carboxy, cycloalkyl of 3 to 7 carbon atoms, b) alkyl, alkenyl, alkynyl, alkoxy and alkylthio of up to 6 carbon atoms and optionally substituted, c) aryl, aralkyl, aralkenyl, aryloxy and arylthio with 1 to 6 alkyl and alkenyl carbon atoms, the aryl being a monocycle of 5 or 6 ring members or condensed rings of 8 to 10 ring members optionally containing at least one heteroatom chosen from oxygen, nitrogen and sulfur and optionally substituted,

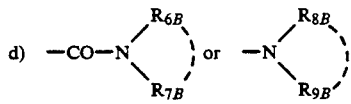

in which either R$_{6B}$ and R$_{7B}$ or R$_{8B}$ and R$_{9B}$ individually are selected from the group consisting of hydrogen, alkyl or alkenyl of up to 6 carbon atoms and optionally substituted by at least one halogen or hydroxyl, alkyl or alkenyl of 2 to 6 carbon atoms substituted by alkoxy of 1 to 6 carbon atoms, aryl or aralkyl with 1 to 6 alkyl carbon atoms, the aryl being a monocycle of 5 or 6 ring members or condensed rings of-8 to 10 ring members optionally containing at least one heteroatom chosen from oxygen, nitrogen and sulfur and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified and esterified carboxy, —(CH$_2$)$_{m1}$-S(O)$_{m2}$-X-R$_{14}$, m$_1$ is an integer from 0 to 4 and m$_2$ is an integer from 0 to 2 and either —X—R$_{14}$ is —NH$_2$, or X is —N—, —NH—CO—, —NH—CO—NH— or a single bond and R$_{14}$ is alkyl, alkenyl or aryl optionally substituted.

or R$_{6B}$ and R$_{7B}$ or R$_{7B}$ and R$_{9B}$ form respectively with the nitrogen atom to which they are attached a monocycle of 5 or 6 ring members or condensed rings of 8 to 10 ring members optionally containing at least one heteroatom chosen from oxygen, nitrogen and sulfur and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified and esterified carboxy, or R$_{8B}$ and R$_{9B}$ individually are acyl of a carboxylic acid of up to 6 carbon atoms, e) —(CH$_2$)$_{m1}$—S(O)$_{m2}$—X—R$_{14}$ as defined above, A$_{1B}$, A$_{2B}$, A$_{3B}$ and A$_{4B}$ are such that one is nitrogen, another is nitrogen or

another is

and the last one is methine substituted by benzyl optionally substituted by at least one substituent with the exception of the substitutents containing an aryl, R$_{4b}$ and R$_{4c}$ individually are chosen from the values of R$_{4B}$, such that R$_{4B}$ is a) hydrogen, hydroxyl, cyano, benzyl, acyl of up to 12 carbon atoms, free, salified and esterified carboxy, cycloalkyl of 3 to 7 carbon atoms, b) alkyl, alkenyl, alkynyl, alkoxy or alkylthio of up to 6 carbon atoms and optionally substituted by at least one of the above substituents with the exception of the substituents having one or two aryl with the proviso that the products of formula I cannot represent the following products in which either R$_{2B}$ and R$_{3B}$ are selected from halogen, hydroxyl, and alkyl and alkoxy and A$_{1B}$, A$_{2B}$, A$_{3B}$ and A$_{4B}$ are such that one is nitrogen, another is methine or nitrogen, another is methine, the methines being optionally substituted by a member selected from the group consisting of free and esterified carboxy and benzyl optionally substituted by alkyl of up to two carbon atoms optionally substituted by hydroxyl or acyloxy, and the last one is benzyl optionally substituted by at least one member of halogen, alkyl, alkoxy, amino, nitro and acetyl, or R$_{2B}$ and R$_{3B}$ are both methoxy, A$_{1B}$ is benzyl substituted by chlorine, A$_{2B}$ is methine substituted by isobutyl or isopropyl, A$_3$ $_B$is nitrogen and A$_{4B}$ is methine, and their non-toxic, pharmaceutically acceptable salts with acids and bases.

Among the preferred compounds of the invention are those of the formula

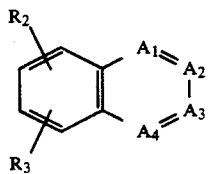

I wherein

R₂ and R₃ individually are selected from the group consisting of a) hydrogen, halogen, hydroxyl, mercapto, cyano, nitro, sulfo, formyl, benzoyl, acyl of up to 12 carbon atoms, free, salified and esterified carboxy and cycloalkyl of 3 to 7 carbon atoms, b) alkyl, alkenyl, alkynyl, alkoxy and alkylthio of up to 6 carbon atoms and optionally substituted, c) aryl, aralkyl, aralkenyl, aryloxy and arylthio with up to 6 alkyl and alkenyl carbon atoms, the aryl being a monocycle of 5 or 6 ring members or condensed rings of 8 to 10 ring members optionally containing at least one heteroatom chosen from oxygen, nitrogen and sulfur, and optionally substituted,

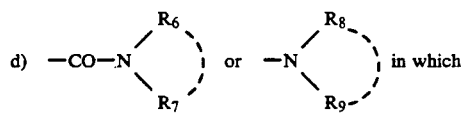

either R₆ and R₇ or R₈ and R₉ individually are selected from the group consisting of hydrogen, alkyl or alkenyl of up to 6 carbon atoms and optionally substituted by at least one member of the group consisting of halogen and hydroxyl, alkyl and alkenyl of 2 to 6 carbon atoms substituted by alkoxy of 1 to 6 carbon atoms, aryl and aralkyl with 1 to 6 alkyl carbon atoms, the aryl being a monocycle of 5 or 6 ring members or condensed rings of 8 to 10 ring members optionally containing at least one heteroatom chosen from oxygen, nitrogen and sulfur, and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified and esterified carboxy, or R₆ and R₇ or R₈ and R₉ form respectively with the nitrogen atom to which they are attached a monocycle of 5 or 6 ring members or condensed rings of 8 to 10 ring members optionally containing at least one heteroatom chosen from oxygen, nitrogen and sulfur and optionally substituted with at least one member of the group consisting of halogen, hydroxyl, cyano, trifluoromethyl, nitro, alkyl, alkenyl, alkoxy, alkylthio and acyl of up to 6 carbon atoms, free, salified and esterified carboxy, or R₈ and R₉ individually are an acyl of a carboxylic acid of up to 6 carbon atoms, A₁, A₂, A₃ and A₄ are such that one is nitrogen, another is nitrogen or

another is

and the last one is methine substituted by benzyl optionally substituted by at least one of the above substituents with the exception of the substituents having an aryl, $R_{4b}$ and $R_{4c}$ individually have the values of R₄, such that R₄ is selected from the group consisting of:

a) hydrogen, hydroxyl, cyano, benzyl, acyl of up to 12 carbon atoms, free, salified and esterified carboxy, cycloalkyl of 3 to 7 carbon atoms, b) alkyl, alkenyl, alkynyl, alkoxy and alkylthio of up to 6 carbon atoms and optionally substituted by at least one substituent above with the exception of the substituents having one or two aryl, it being understood that the products of formula I cannot be the following products wherein:

either R₂ and R₃ are selected from halogen, hydroxyl, alkyl and alkoxy and A₁, A₂, A₃ and A₄ are such that: one is nitrogen, another is methine or nitrogen, another is methine, the methines being optionally substituted by free or esterified carboxy or benzyl optionally substituted by alkyl of 1 to two carbon atoms optionally substituted by hydroxyl or acyloxy, and the last is benzyl optionally substituted by at least one of halogen, alkyl, alkoxy, amino, nitro and acetyl, or R₂ and R₃ are both methoxy, A₁ is benzyl substituted by chlorine, A₂ is methine substituted by isobutyl or isopropyl, A₃ is nitrogen and A₄ is methine.

In the products of formula I and in what follows: halogen preferably is chlorine, but can also be fluorine, bromine or iodine and the term acyl preferably has up to 7 carbon atoms such as acetyl, propionyl, butyryl or benzoyl, but can also be valeryl, hexanoyl, acryloyl, crotonoyl or carbamoyl as well. The term acyloxy includes compounds in which the acyl has the above meaning and for example acetoxy or propionyloxy.

The term esterified carboxy preferably means a lower alkyl-carbonyl such as methoxycarbonyl, ethoxycarbonyl, tert-butoxycarbonyl or benzyloxycarbonyl and the term cycloalkyl is preferably cyclopropyl, cyclopentyl or cyolohexyl but also cyclobutyl. The term linear or branched alkyl preferably includes methyl, ethyl, n-propyl, isopropyl, n-butyl, isobutyl, sec-butyl and tert-butyl but can also be hexyl or pentyl, particularly isopentyl and isohexyl. The term linear or branched alkenyl is preferably vinyl, allyl, 1-propenyl, butenyl and particularly buten-1-yl, or pentenyl.

The term linear or branched alkynyl is preferably ethynyl, propargyl, butynyl or pentynyl and the term linear or branched alkoxy is preferably methoxy or ethoxy, but can also be propoxy, isopropoxy, linear, secondary or tertiary butoxy. The term linear or branched alkylthio includes alkyl which can be the values indicated above for alkyl. The alkylthio is preferably methylthio or ethylthio, but can also be propylthio, isopropylthio, n-butylthio, sec-butylthio, tert-butylthio, isopentylthio or isohexylthio.

The term aryl includes carbocyclic or heterocyclic monocycles or condensed rings which can contain one or more heteroatoms chosen from oxygen, nitrogen or sulfur and when these heterocyclic contain more than one heteroatom, the heteroatoms of these heterocyclic can be identical or different. The monocycle preferably has 5 or 6 ring members and includes a carbocyclic monocycle such as phenyl.

Among the heterocyclic monocycles are thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl such as delta 2-pyrrolinyl, imidazolinyl such as delta 2-imidazolinyl, pyrazolinyl such as delta 3-pyrazolinyl as well as the isomers of position of the heteroatom or heteroatoms that these can contain such as, for example, isothiazolyl or isoxazolyl.

The condensed rings preferably have 8 to 14 ring members. Among the carbocyclic condensed rings are naphthyl and phenanthryl and among the heterocyclic condensed rings are benzothienyl, naphtho-[2,3-b]-thienyl, indanyl, indenyl, thianthrenyl, isobenzofurannyl, chromenyl, xanthenyl, phenoxathiinyl, indolazinyl, isoindolyl, 3H-indolyl, indolyl, indazolyl, purinyl, quinolizinyl, isoquinolyl, quinolyl, phthalazinyl, naphthyridinyl, imidazopyridyl, pyrimidinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, or also condensed polycyclic systems constituted by heterocyclic monocycles as defined such as furo-[2,3-b]-pyrrole or thieno-[2,3-b]-furane.

Examples of aryl are phenyl, naphthyl, thienyl such as thien-2-yl and thien-3-yl, furyl such as fur-2-yl, pyridyl such as pyrid-3-yl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl; condensed heterocycles having at least one heteroatom chosen from sulfur, nitrogen and oxygen are benzothienyl such as benzothien-3-yl, benzofuryl, benzopyrrolyl, benzimidazolyl, benzoxazolyl, thionaphthyl, indolyl or purinyl.

Such aryls are optionally substituted such as N-substituted pyrrolyl like N-methylpyrrolyl, substituted 3- or 4-isoxazolyl, such as 3-aryl-5-methylisoxazol-4-yl, the aryl being phenyl or halophenyl. Aralkyl and aralkenyl have the alkyl, alkenyl and aryl respectively as defined above for these groups. Examples of aralkyl are benzyl, diphenylmethyl, triphenylmethyl, naphthylmethyl, indenylmethyl, thienylmethyl such as thien-2-yl-methyl, furylmethyl such as furfuryl, pyridylmethyl, pyrimidylmethyl or pyrrolylmethyl, it being understood that in the non-exhaustive list of examples as mentioned above, the alkyl can also be ethyl, propyl or butyl such as in phenethyl.

Examples of aralkenyl are those where alkyl is replaced by alkenyl such as phenylvinyl or phenylallyl, it being understood that the phenyl can also be replaced by naphthyl, pyridyl or one of the aryls as defined above in the non-exhaustive list of the aralkyls. The tems aryloxy and arylthio are those in which the aryl can have the values defined above and in a non-exhaustive manner examples of such aryloxy and arylthio include phenoxy, naphthyloxy, pyridyloxy, phenylthio and naphthylthio.

In the products of formula I and in what follows, the monocyclic and condensed rings are aryls which are unsaturated carbocyclics or heterocyclics as defined above, but also includes saturated heterocyclics as defined above and can contain one or more heteoatoms chosen from oxygen, nitrogen or sulfur and when these heteocyclics contain more than one heteroatom, the heteroatoms of these heterocyclic can be identical or different. Among the saturated heterocyclic monocyclics are pyrrolidinyl, imidazolidinyl, pyrazolidinyl, piperidyl, piperazinyl or morpholinyl and among the saturated heterocyclic of condensed rings are 1,10-diaza-4-anthryl.

The amino that can be represented by one or more of the optional substituents defined in the products of formula I and in what follows are those of the formula

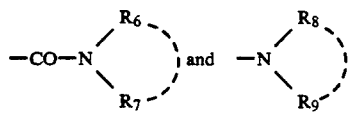

in which $R_6$ and $R_7$ or $R_8$ and $R_9$ are individually selected from the group consisting of hydrogen; alkyl as defined above to give preferably monoalkyl- or dialkylamino in which the alkyl has 1 to 6 carbon atoms and particularly methyl, ethyl, isopropyl, trifluoromethyl, pentafluoroethyl, hydroxymethyl, hydroxyethyl, methoxymethyl, methoxyethyl, ethoxyethyl; alkenyl as defined above and preferably vinyl and allyl; aryl or aralkyl as defined above, carbocyclic or heterocyclic, and particularly phenyl, benzyl, phenethyl, naphthyl, indolyl, indolinyl, thienyl, furyl, pyrrolyl, pyridyl, pyrrolidinyl, piperidino, morpholino, piperazinyl optionally substituted by one or more substituent as defined above such as methylpiperazinyl, fluoromethylpiperazinyl, ethylpiperazinyl, propylpiperazinyl, phenylpiperazinyl or benzylpiperazinyl.

When $R_6$ and $R_7$ on the one hand or $R_8$ and $R_9$ on the other hand form a heterocycle with the nitrogen atom to which they are attached, it may be pyrrolyl, imidazolyl, pyridyl, pyrazinyl, pyrimidyl, indolyl, indolinyl, purinyl, quinolyl, pyrrolindinyl, piperidyl, piperidino, morpholino, piperazinyl, all optionally substituted by the substituents mentioned above and particularly by one or more chosen from chlorine and fluorine, methyl, ethyl, isopropyl, tert-butyl, methoxy, ethoxy, propoxy, benzoyl, methoxycarbonyl and ethoxycarbonyl such as methylpiperazinyl, ethylpiperazinyl, propylpiperazinyl, phenylpiperazinyl or benzylpiperazinyl: in these last two, phenyl and benzyl can be substituted as indicated above for aryl, aralkyl and aralkenyl.

The acyl of $R_8$ and $R_9$ are as defined previously and can be chosen from acetyl, propionyl, butyryl, valeryl or carbamoyl.

The addition salts with mineral or organic acids of the products of formula I can be the salts formed with the following acids: hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid oxalic acid, glyoxylic acid, aspartic acid, ascorbic acid, alkanemcnosulfonic acids such as methanesulfonic acid, ethanesulfonic acid, propanesulfonic acid, alkanedisulfonic acids such as methanedisulfonic acid, $\alpha,\beta$-ethanedisulfonic acid, arylmonosulfonic acids such as benzenesulfonic acid and aryldisulfonic acid.

The carboxys of the products of formula I can be salified by mineral bases such as an equivalent of sodium, potassium, lithium, calcium, magnesium or ammonium or organic bases such as methylamine, propylamine, trimethylamine, diethylamine, triethylamine, N,N-dimethylethanolamine, tris(hydroxymethyl) amino methane, ethanolamine, pyridine, picoline, dicyclohexylamine, morpholine, benzylamine, procaine, lysine, arginine, histidine and N-methylglucamine.

The alkyl, alkenyl and alkynyl as defined above as well as the alkyl or alkenyl of the alkylthio, aralkyl and aralkenyl as defined above can be non-substituted or carry one or more substituents chosen from the group of halogen such as chloro or bromo, as in 2-bromoethyl; hydroxyl; aryl as defined above such as carbocyclic or heterocyclic monocycle or condensed rings, it being understood that the heterocyclics as defined above can contain one or more heteroatoms chosen from oxygen, nitrogen or sulfur and that when these heterocyclics contain more than one heteroatom, the heteroatoms can be identical or different, the heterocyclic being able to be linked by a carbon atom or, if appropriate, by nitrogen; aralkyl in which the aryl is as defined above; cycloalkyl such as cyclopropyl, cyclopentyl or cyclohexyl; cycloalkenyl such as cyclohexenyl optionally substituted, among which there can be mentioned 1,3-dimethyl cyclohexene; alkoxy as defined above such as methoxy, ethoxy, n-propoxy or isopropoxy as in methoxymethyl or 1-ethoxyethyl; substituted alkoxy such as (trihaloalkyl)-oxy such as trifluoromethoxy; aryloxy for example phenoxy; (aryalkyl)-oxy, for example benzyloxy; mercapto; alkylthio such as methylthio or ethylthio; substituted alkylthio such as trihaloalkylthio such as for example, trifluoromethylthio; arylthio; aralkylthio; amino for example 2-aminoethyl; amino substituted by one or two members from alkyl, alkenyl, aryl and aralkyl as defined above such as monoalkylamino i.e. methylamino or ethylamino, dialkylamino such as dimethylamino; nitro; cyano; azido; carboxy; esterified carboxy such as methoxycarbonyl or ethoxycarbonyl; formyl; acyl such as acetyl, propionyl or benzoyl; acyl substituted for example by an amino as defined above or by a cyclic linked to the acyl by a nitrogen atom, this cyclic being able to contain optionally one or more heteroatoms chosen from nitrogen, oxygen or sulfur and substituted as defined above; acyloxy, for example acetoxy or propionyloxy; carbamoyl; substituted carbamoyl, for example lower N-monoalkyl carbamoyl such as N-methylcarbamoyl, N-ethylcarbamoyl, lower N,N-dialkylcarbamoyl such as N,N-dimethylcarbamoyl, N,N-diethylcarbamoyl; N-(lower hydroxyalkyl) carbamoyl such as N-(hydroxymethyl)-carbamoyl, N-(hydroxyethyl)-carbamoyl, a lower carbamoylalkyl such as carbamoylmethyl, carbamoylethyl; phthalimido; acylamido for example acetamido or benzamido; alkoxycarbonylamino, for example methoxycarbonylamino or ethoxycarbonylamino; or (aralkyl)-oxycarbonylamino, for example benzyloxycarbonylamino.

The aryl and alkoxy as defined above and aryl of the aralkyl and aralkenyl as defined above can be non-substituted or carry one or more substituents chosen from the list indicated above for the optional substituents of alkyl, alkenyl and alkynyl as defined above such as o-chloro-phenyl, but can also be substituted by one or more members chosen from the group formed by alkyls such as lower alkyl, for example methyl, ethyl, isopropyl or tert-butyl; alkenyl; substituted alkyl such as trihaloalkyl as in trifluoromethyl; alkenyl such as vinyl or allyl; alkynyl such as propargyl.

Among the preferred products of formula $I_B$ and I are those wherein the individual substituents that can be carried by: a) alkyl, alkenyl, alkynyl, alkoxy and alkylthio of $R_{2B}$, $R_{3B}$, $R_2$ and $R_3$ b) aryl, aralkyl, aralkenyl, aryloxy and arylthio of $R_{2B}$, $R_{3B}$, $R_2$ and $R_3$, c) the alkyl, alkenyl and aryl of $R_{14}$ are selected from the group consisting of halogen, hydroxyl, cyano, nitro, formyl, acyl and acyloxy of up to 6 carbon atoms, benzoyl, carboxy free, salified or esterified by alkyl of 1 to 6 carbon atoms, alkyl and alkenyl of up to 6 carbon atoms and optionally substituted by at least one substituent chosen from halogen, hydroxyl and alkoxy of 1 to 6 carbon atoms, alkoxy and alkylthio of up to 6 carbon atoms, aryl and aralkyl in which the alkyls have up to 6 atoms, the aryl being a monocyclic of 5 or 6 ring members or condensed rings of 8 to 10 ring members optionally containing one or more heteroatoms chosen from oxygen, nitrogen and sulfur, and being substituted by one or more of halogen, hydroxyl, cyano, trifluoromethyl, nitro, alkyl, alkenyl, alkoxy and acyl of up to 6 carbon atoms, free, salified or esterified carboxy,

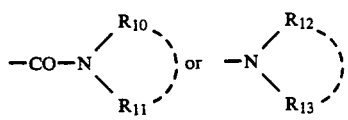

in which
either $R_{10}$ and $R_{11}$ or $R_{12}$ and $R_{13}$ are individually selected from the group consisting of hydrogen, alkyl or alkenyl of up to 6 carbon atoms and optionally substituted by at least one halogen or hydroxyl, alkyl or alkenyl of 2 to 6 carbon atoms substituted by alkoxy of 1 to 6 carbon atoms, aryl or arylalkyl in which the alkyl has 1 to 6 carbon atoms and aryl is a monocycle of 5 or 6 ring members or condensed rings of 8 to 10 ring members optionally containing one or more heteroatoms chosen from oxygen, nitrogen and sulfur and optionally substituted by one or more member selected from the group consisting of halogen, hydroxyl, cyano, trifluoromethyl, nitro, alkyl, alkenyl, alkoxy and acyl of up to 6 carbon atoms, free, salified and esterified carboxy, or $R_{10}$ and $R_{11}$ or $R_{12}$ and $R_{13}$ form respectively with the nitrogen to which they are attached a monocycle of 5 or 6 ring members or condensed rings of 8 to 10 ring members optionally containing one or more heteroatoms chosen from oxygen, nitrogen and sulfur and optionally substituted by at least one member chosen from halogen, hydroxy, cyano, trifluoromethyl, nitro, alkyl, alkenyl, alkoxy and acyl of up to 6 carbon atoms, free, salified or esterified carboxy, or $R_{12}$ and $R_{13}$ individually or one of $R_{10}$ and $R_{11}$ is acyl of a carboxylic acid of up to 6 carbon atoms, the said products of formulae $I_B$ and I being in all possible racemic, enantiomeric and diastereoisomeric isomer forms, as well as their addition salts with mineral and organic acids or with mineral and organic bases.

The 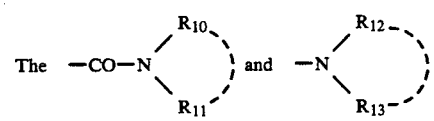

as defined above can have respectively the same values as those defined of

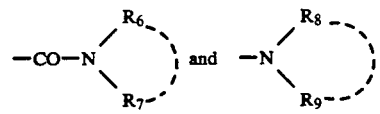

Among the substituents that can be on alkyl, alkenyl, alkynyl, alkoxy, alkylthio, aryl, arylalkyl and arylalkenyl as defined above are more particularly halogen such as chloro and bromo; hydroxyl; acyl such as acetyl, propionyl, butyryl, valeryl, hexanoyl, acryloyl, crotonoyl or carbamoyl; benzoyl; esterified carboxy preferably lower alkoxycarbonyl such as methoxycarbonyl, ethoxycarbonyl or benzyloxycarbonyl; alkyl such as methyl or ethyl; amino; substituted amino such as monoalkyl- and dialkylamino, i.e. methylamino, ethylamino or dimethylamino; alkoxy, for example methoxy, ethoxy or isopropoxy; aryl such as phenyl, biphenyl, naphthyl, indenyl, indolyl or indolinyl; aralkyl such as benzyl or phenethyl; alkyl, alkoxy and aryl as defined above substituted by one or more, members chosen from the group consisting of hydroxy, alkyl and alkoxy such as methyl, ethyl, tert-butyl, methoxy, ethoxy, isopropoxy; substituted amino such as monoalkyl- and dialkylamino, i.e. methylamino, ethylamino or dimethylamino; carbocyclic or heterocyclic monocycles of 6 ring members such as phenyl, pyrannyl, pyridyl, pyrimidinyl, pyridazinyl, pyrazinyl, piperidyl, piperazinyl, piperidino and morpholino; carbocyclic or heterocyclic monocycles of 5 ring members, such as furyl, pyrrolyl, pyrrolinyl, imidazolyl or pyrazolyl, isothiazolyl, isoxazolyl, pyrrolidinyl, imidazolidinyl, pyrazolidinyl; carbocyclic or heterocyclic condensed rings such as naphthyl, indolyl, quinolyl or purinyl as well as their position isomers of the heteroatom or heteroatoms, for example of nitrogen such as indazolyl or isoquinolyl.

When such heterocyclics contain one or more nitrogen atoms, this/these nitrogen atom(s) cannot be substituted or one or more of these nitrogen atoms can be substituted, for example, alkyl or alkoxy of 1 to 5 carbon atoms, as defined above such as methyl, ethyl, isopropyl, tert-butyl, methoxy or ethoxy, phenyl or benzyl optionally substituted by the substituents already mentioned above for aryl and aralkyl such as methylpiperazinyl, ethylpiperazinyl, propylpiperazinyl, phenylpiperazinyl or benzylpiperazinyl.

Among the particularly preferred values of such groups are phenyl, naphthyl, pyridyl, piperazinyl, pyrimidinyl, pyridazinyl and pyrazinyl.

Such products of formula $I_B$ thus are in particular derivatives: of quinoline in which one of $A_1$ and $A_4$ is nitrogen, of isoquinoline in which one of $A_2$ and $A_3$ is nitrogen, and derivatives: of cinnoline in which $A_1$ and $A_2$ or $A_3$ and $A_4$ both are nitrogen, of quinoxaline in which $A_1$ and $A_4$ are nitrogen and of quinazoline in which $A_1$ and $A_3$ or $A_2$ and $A_4$ both are nitrogen.

The $-(CH_2)_{m1}-S(O)_{m2}-X-R_{14}$ as defined above are these wherein $(CH_2)_{m1}$ has the values of alkylene such as methylene, ethylene, n-propylene or n-butylene and $R_{14}$ is alkyl or alkenyl chosen from the values defined above or aryl also chosen from the values indicated above such as phenyl, biphenyl, naphthyl, tetrazolyl. The alkyl or alkenyl of $R_{14}$ can optionally be substituted by aryl chosen from the values, defined above to form an aralkyl or aralkenyl.

These alkyl, alkenyl, aryl, aralkyl and aralkenyl can be substituted as indicated above for these radicals. There can be mentioned for example and in a nonexhaustive manner:

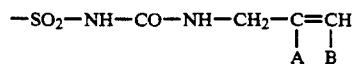

—$SO_2$—NH—$CH_3$, —$SO_2$—NH—$CF_3$,

—$SO_2$—NH—$C_6H_5$, —$SO_2$NH—$CH_2$—$C_6H_5$,

—$CH_2$—$SO_2$—$NH_2$, —$CH_2$—$SO_2$—NH—$C_6H_5$,

—$SO_2$—NH—CO—NH—$CH_3$,

—$SO_2$—NH—CO—NH—$C_6H_5$,

—$SO_2$—NH—CO—NH—$CF_3$,

—$SO_2$—NH—CO—NH—$CH_2$—$C_6H_5$,

—$SO_2$—NH—CO—NH—$C_6H_4Cl$,

—$SO_2$—NH—CO—NH—$CH_2$—$C_6H_3Cl_2$,

—$SO_2$—NH—CO—NH—CH=CH—$CH_3$,

-continued

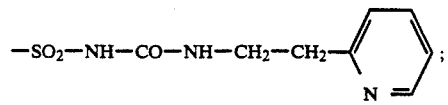

in which A and B individually are chosen from hydrogen, phenyl, pyridyl and pyrimidyl

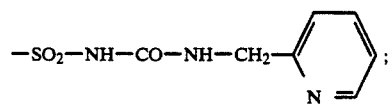

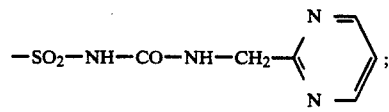

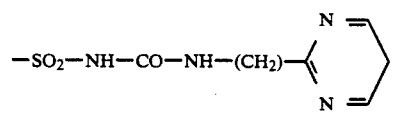

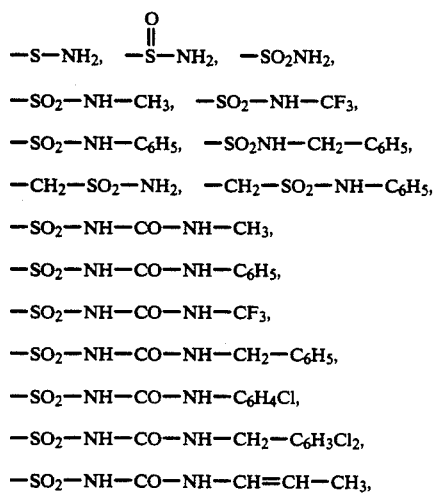

The aryl of $Y_1$ can be substituted by one or more members chosen from the values of $R_2$ and $R_3$ and particularly by —NH—$(CH_2)_m$—$SO_2$—X—$R_{14}$ and —CO—NH—$(CH_2)_m$—X—$R_{14}$ in which $(CH_2)_m$—$SO_2X$—$R_{14}$ can have the values indicated above. There can be mentioned in a non-exhaustive manner —NH—$SO_2$—$CH_3$, —NH—$SO_2$—$C_6H_5$, —NH—$SO_2$—$CF_3$, —NH—$CH_2$—$SO_2$—NH—$C_6H_5$, —CO—NH—$SO_2$—$C_2H_5$, —CO—NH—$SO_2$—$CH_3$ and —CO—NH—$SO_2$—$CH_2$—$C_6H_5$ A particular subject of the invention is the products of formula $I_B$ wherein the individual substituent or substituents that can be carried by a) alkyl, alkenyl, alkynyl, alkoxy and alkylthio of $R_{4B}$ and b)

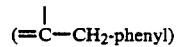

(=C—$CH_2$-phenyl).

of one of $A_{1B}$, $A_{2B}$, $A_{3B}$ or $A_{4B}$, are chosen from the group formed by halogen, hydroxyl, cyano, nitro, formyl, acyl and acyloxy of up to 6 carbon atoms, carboxy free, salified or esterified by alkyl of 1 to 6 carbon atoms, alkyl and alkenyl of up to 6 carbon atoms and optionally substituted by one or more substituents chosen from halogen, hydroxy and alkoxy of 1 to 6 carbon atoms, alkoxy and alkylthio of 1 to 6 carbon atoms,

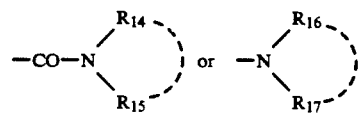

in which $R_{14}$ and $R_{15}$ or $R_{16}$ and $R_{17}$ individually are selected from the group consisting of hydrogen, alkyl or alkenyl of up to 6 carbon atoms and optionally substituted by one or more halogen and hydroxyl, alkyl or alkenyl of 2 to 6 carbon atoms substituted by alkoxy of 1 to 6 carbon atoms, and $R_{16}$ and $R_{17}$ individually are an acyl of a carboxylic acid of up to 6 carbon atoms, the said products of formula $I_n$ being in all possible racemic, enantiomeric ducts of formula $I_B$ being in all possible racemic, enantiomeric and diastereoisomeric isomer forms, as well as their addition salts with mineral and organic acids or mineral and organic bases.

A more particular subject of the invention is the products of the formula

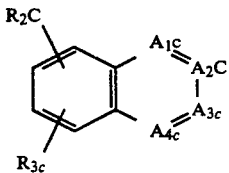

$I_c$ in which:

$R_{2c}$ and $R_{3c}$ individually are selected from the group formed by hydrogen, halogen, hydroxyl, mercapto, cyano, nitro, formyl, benzoyl, acyl of up to 6 carbon atoms, carboxy, free, salified or esterified by alkyl of 1 to 4 carbon atoms, alkyl, alkenyl, alkoxy and alkylthio of up to 6 carbon atoms, phenyl, naphthyl, benzyl and phenylthio, all these optionally substituted by one or more members of the group halogen, hydroxyl, alkoxy of 1 to 4 carbon atoms, tri-fluoromethyl, cyano, acyl, free, salified or esterified carboxy, tetrazole, isoxazole, pyrrolidinyl, pyrrolidinylcarbonyl and phenyl optionally substituted by one or more chosen from halogen, hydroxyl and alkyl and alkoxy of 1 to 4 carbon atoms, amino, mono- or dialkylamino, carbamoyl, pyrrolyl, morpholino, piperazinyl, pyrrolylmethyl, morpholinomethyl, piperazinylmethyl, pyrrolylcarbonyl, morpholinocarbonyl, pyrrolidinylcarbonyl, piperazinylcarbonyl, all the piperazinyl being optionally substituted on the second nitrogen atom by alkyl or phenyl optionally substituted by one or more chosen from halogen, hydroxyl, nitro, alkyl, alkoxy or acyl of 1 to 4 carbon atoms, trifluoromethyl, cyano, free, salified or esterified carboxy, tetrazole and isoxazole, $A_{1c}$, $A_{2c}$, $A_{3c}$ and $A_{4c}$ are such that: one is nitrogen, another is nitrogen or methine substituted by $R_{4ab}$, another is methine substituted by $R_{4ac}$, and the last one is methine substituted by optionally substituted benzyl, $R_{4ab}$ and $R_{4ac}$ individually are chosen from the values of $R_4$, such that $R_{4a}$ is selected from the group consisting of hydrogen, hydroxyl, cyano, carboxy, free, salified or esterified by alkyl of 1 to 4 carbon atoms, alkyl, alkenyl, alkoxy, acyl or alkylthio of up to 7 carbon atoms, all being optionally substituted by one or more members chosen from halogen, hydroxyl, nitro, alkyl, alkoxy or acyl of up to 4 carbon atoms, trifluoromethyl, cyano, carboxy, free, salified or esterified by alkyl of 1 to 4 carbon atoms, it being understood that the products of formula $I_a$ cannot be the following products:

either $R_{2c}$ and $R_{3c}$ are chosen from halogen, hydroxyl, alkyl and alkoxy and $A_{1c}$, $A_{2c}$, $A_{3c}$ and $A_{4c}$ are such that: one is nitrogen, another is methine or nitrogen, another is methine, the two methines optionally substituted by a member chosen from the free or esterified carboxy, benzoyl, phenyl optionally substituted by alkyl of 1 to two carbon atoms optionally substituted by hydroxyl or acyloxy, and the last one is benzyl optionally substituted by one or more members chosen from halogen, alkyl, alkoxy, amino, nitro and acetyl or $R_{2c}$ and $R_{3c}$ are both methoxy, $A_{1c}$ is benzyl substituted by chlorine, $A_{2c}$ is methine substituted by isobutyl or isopropyl, $A_{3a}$ is nitrogen and $A_{4c}$ is methine, the said products of formula $I_c$ being in all possible racemic, enantiomeric and diastereoisomeric isomer forms, as well as their addition salts with mineral and organic acids or mineral and organic bases.

A more particular subject of the invention are the products of the formula

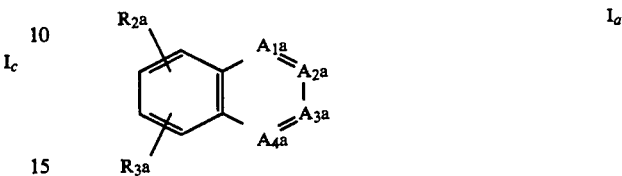

$I_a$ in which: $R_{2a}$ and $R_{3a}$ individually are chosen from the group formed by: hydrogen, halogen, hydroxyl, mercapto, cyano, nitro, formyl, benzoyl, acyl of up to 6 carbon atoms, carboxy, free, salified or esterified by alkyl of 1 to 4 carbon atoms, alkyl, alkoxy and alkylthio of 1 to 6 carbon atoms, phenyl, naphthyl, benzyl and phenylthio, all optionally substituted by one or more members chosen from halogen, hydroxyl, alkoxy of up to 4 carbon atoms, trifluoromethyl, cyano, acyl, free, salified or esterified carboxy, tetrazole and isoxazole, amino. mono- or dialkylamino, carbamoyl, pyrrolyl, morpholino, piperazinyl, pyrrolymethyl, morpholinomethyl, piperazinylmethyl, pyrrolylcarbonyl, morpholinocarbonyl, piperazinycarbonyl, all the piperazinyl being optionally substituted on the second nitrogen atom by alkyl or phenyl optionally substituted by one or more member chosen from halogen, hydroxyl, nitro, alkyl, alkoxy and acyl of 1 to 4 carbon atoms, trifluoromethyl, cyano, free, salified or esterified carboxy, tetrazole and isoxazole, $A_{1a}$, $A_{2a}$, $A_{3a}$ and $A_{4a}$ are such that one is nitrogen, another is nitrogen or methine substituted by $R_{4ab}$, another is methine substituted by $R_{4ac}$, and the last one methine substituted by optionally substituted benzyl, $R_{4ab}$ and $R_{4c}$ individually are chosen from the values of $R_{4a}$, such that $R_{4a}$ is selected from the group consisting of hydrogen, hydroxyl, cyano, carboxy, free, salified or esterified by alkyl of 1 to 4 carbon atoms, alkyl, alkenyl, alkoxy, acyl or alkylthio of up to 7 carbon atoms, all optionally substituted by one or more members chosen from halogen, hydroxyl, nitro, alkyl, alkoxy and acyl of up to 4 carbon atoms, trifluoromethyl, cyano, carboxy, free, salified or esterified by alkyl of 1 to 4 carbon atoms, it being understood that the products of formula $I_a$ cannot be the following products: either $R_{2a}$ and $R_{3a}$ are chosen from halogen, hydroxyl and alkyl and alkoxy and $A_{1a}$, $A_{2a}$, $A_{3a}$ and $A_{4a}$ are such that one is nitrogen, another is methine or nitrogen, another is methine, these two methines being optionally substituted by a member chosen from the free or esterified carboxy, benzoyl, phenyl optionally substituted by alkyl of 1 to most two carbon atoms optionally substituted by hydroxyl or acyloxy, and the last is benzyl optionally substituted by one or more members chosen from halogen atoms, alkyl, alkoxy, amino, nitro and acetyl or $R_{2a}$ and $R_{3a}$ are both methoxy, $A_{1a}$ is benzyl substituted by chlorine, $A_{2a}$ is methine substituted by isobutyl or isopropyl, $A_{3a}$ is nitrogen and $A_{4a}$ is methine, the said products of formula $I_a$ being in all possible racemic, enantiomeric and diastero-isomeric isomer forms, as well as their addition salts with mineral and organic acids or mineral and organic bases.

Among the products which are a subject of the invention, are those of formula $I_B$ in which $R_{2B}$ and $R_{3B}$ are hydrogen, $A_{1B}$, $A_{2B}$ and $A_{3B}$ are such that one or two of them are nitrogen, and the others individually are

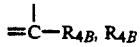

is chosen from hydrogen, n-butyl and alkylthio of 1 to 4 carbon atoms, and $A_{4B}$ is methine substituted by benzyl optionally substituted by one or more members chosen from cyano and free, salified and esterified carboxy, the said products of formula $I_B$ being in all possible racemic, enantiomeric and diastereoisomeric isomer forms, as well as their addition salts with mineral and organic acids or mineral and organic bases.

The novel process of the invention for the preparation of the compounds of formula $I_B$ comprises either reacting a compound of the formula

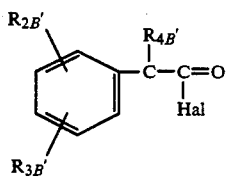

III in which $R_{2B'}$, $R_{3B'}$ and $R_{4B'}$ have the meanings indicated above respectively for $R_{2B}$, $R_{3B}$ and $R_{4B}$ in which the optional reactive functions are optionally protected by protective groups and Hal is halogen in a substitution reaction to obtain a compound of the formula

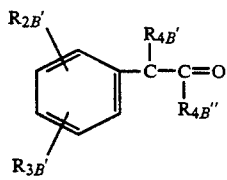

IV in which $R_{2B'}$, $R_{3B'}$ and $R_{4B'}$ have the meanings above and $R_{4B'}$, identical to or different from $R_{4B'}$, has the meaning indicated above for $R_{4B}$ in which the optional reactive functions are optionally protected by protective groups reacting the latter with a compound of the formula

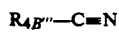

V in which $R_{4B'''}$, identical to or different from $R_{4B'}$ or $R_{4B''}$, has the meaning indicated above for $R_{4B}$ in which the optional reactive functions are optionally protected by protective groups to obtain after cyclization a product of the formula

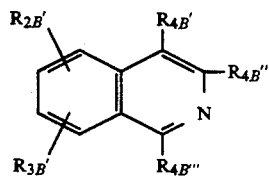

$I_i$ in which $R_{B'}$, $R_{3B'}$, $R_{4B'}$, $R_{4B''}$ and $R_{4B'''}$ have the meanings above b) or reacting a product of the formula

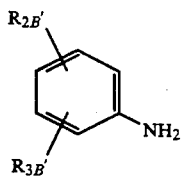

VI in which $R_{2B'}$ and $R_{3B'}$ have the meanings above with a product of the formula

VII in which $R_{4B'}$ and $R_{4B''}$, identical or different, have the meanings indicated above, and alk is alkyl of 1 to 6 carbon atoms to obtain a compound of the formula

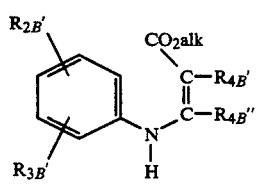

VIII in which $R_{2B'}$, $R_{3B'}$, $R_{4B'}$, $R_{4B''}$ and alk have the meanings above, cyclizing the latter to obtain the compound of the formula

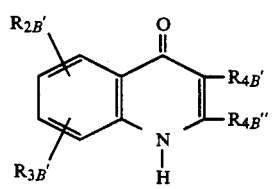

$II_b$ in which $R_{2B'}$, $R_{3B'}$, $R_{4B'}$ and $R_{4B''}$ have the meanings above, c) or reacting a product of the formula

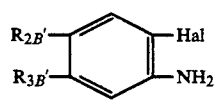

IX in which $R_{2B'}$ and $R_{3B'}$ have the meanings above with a product of the formula

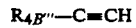

X in which $R_{4B'''}$ has the meaning above to obtain a compound of the formula

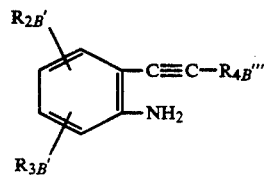

XI in which $R_{2B'}$, and $R_{3B'}$ and $R_{4B'''}$ have the meanings above, subjecting the latter to a cyclization reaction in the presence of a nitrogen donor such as sodium nitrite to obtain a product of the formula

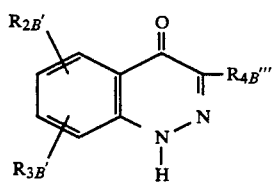

in which R$_{B'}$, R$_{3B'}$and R$_{4B'''}$have the meanings above
d) or reacting a product of the formula

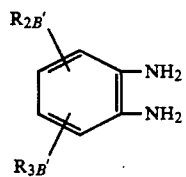

in which R$_{2B'}$and R$_{3B'}$have the meanings above with a product of the formula R$_{4B'}$—CO—CO$_2$alk      XIII in which R$_{4B'}$has the meaning above, and alk is alkyl or 1 to 6 carbon atoms to obtain, after cyclization, a product of the formula

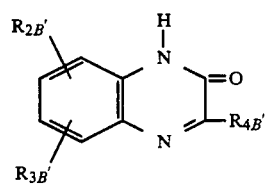

in which R$_{2B'}$, R$_{3B'}$and R$_{4B'}$have the meanings above,
e) or reacting a product of the formula

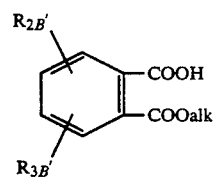

in which R$_{2B'}$, R$_{3B'}$and alk have the meanings above, after, if desired, a halogenation reaction of the free, carboxy function, is subjected to an addition reaction on this carboxy function of a compound of formula R$_{4B'}$, R$_{4B'}$having the meaning indicated above to obtain, after cyclization in the presence of hydrazine or a derivative a product of the formula

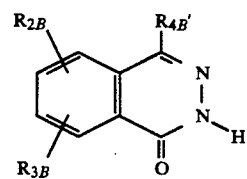

in which R$_{2B'}$, R$_{3B'}$and R$_{4B'}$have the meanings above
f) or reacting a product of the formula

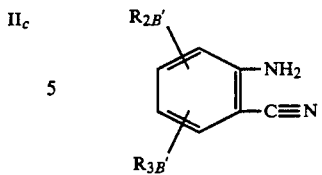

in which R$_{2B'}$and R$_{3B'}$have the meanings above with a product of the formula

R$_{4B'}$—CO—C      XVI in which R$_{4B'}$has the meaning above to obtain a product of the formula

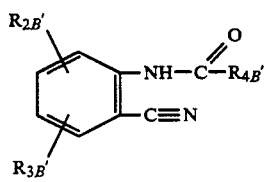

in which R$_{2B'}$, R$_{3B'}$and R$_{4B'}$have the meanings previously indicated to obtain after cyclization a product of the formula

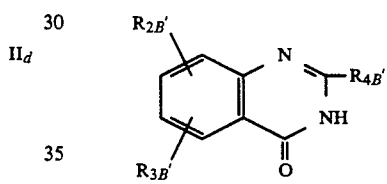

in which R$_{2B'}$, R$_{3B'}$and R$_{4B'}$have the meanings above, which products of formula I$_i$ can be the products of formula I$_B$ and the products of formulae II$_b$, II$_c$, II$_d$, II$_e$ and II$_f$ as defined above which can be the products of formula I$_B$ in which at least one of A$_{1B}$, A$_{2B}$, A$_{3B}$ and A$_{4B}$ is methine carrying a hydroxyl, which are subjected, if desired and if necessary, to one or more of the following reactions in any order:

a complete reduction reaction of the hydroxyl or oxo to methine followed by an aromatization, on the products of formula I$_i$ in which one of R$_{4B'}$, R$_{4B''}$or R$_{4B'''}$is hydroxyl or on the products of formulae II$_b$, II$_c$, II$_d$, II$_e$ and II$_f$, either firstly, to a substitution reaction of the hydroxyl by halogen followed by the action of a product of the formula R$_{p4}$ - M - Hal in which R$_{p4}$ has the meaning indicated above for R$_4$ in which the optional reactive functions are optionally protected by protective groups, M is a metal atom chosen from magnesium, copper and zinc and Hal is halogen, or to the action of a product of formula R$_{p4}$ - Hal in which Hal is a halogen, to obtain the corresponding products of formula I$_B$, a conversion reaction of an oxo function into a=S function, an elimination reaction of the protective groups which can be carried by the protected reactive functions, a salification reaction by a mineral or organic acid or a mineral or organic base to obtain the corresponding salt, an esterification reaction of an acid function, a saponification reaction of an ester function into an acid function, a conversion reaction of an alkoxy function into a hydroxyl function, a con-version reaction of a cyano into an acid function, a reduction reaction of the carboxy function to an alcohol function, a resolution reaction of the racemic forms, the said products of formula $I_B$ thus obtained being in all possible racemic, enantiomeric and diastereoisomeric isomer forms.

In a preferred mode of the above process, the substitution reaction on the halogen derivative of formula III to obtain the product of formula IV can be carried out by the usual methods known to a man skilled in the art such as by the reaction of an organometal such as an organozinc of formula $Zn-Br-R_{4B''}$ on the acid chloride of formula III or also, particularly when $R_{4B''}$ is butyl by the reaction of a tin derivative such as the compound of formula $(R_{4B''})_4 Sn$ preferably in the presence of palladium in a solvent such as ether or tetrahydrofuran.

The addition reaction of the compound of formula V on the compound of formula IV can be carried out by the usual methods known such as in phosphoryl trichloride in the presence of a Lewis acid and the cyclization reaction giving the product of formula Ii takes place in situ. The addition reaction of the compound of formula VII on the compound of formula VI can be carried out by the usual methods known such as in the presence of a desiccating agent such as a molecular sieve or also an acid such as p-toluene sulfonic acid. The cyclization reaction of the compound of formula VIII into the compound of formula $II_b$ can be carried out in a solvent such as DOWTHERM$_R$ or also in the absence of a solvent by taking the compound to its melting point.

The addition reaction of the compound of formula X onto the compound of formula IX to obtain the compound of formula XI can be carried out in the presence of a cuprous salt, preferably in the presence of a catalyst such as a palladium catalyst in a basic solvent such as triethylamine or diethylisopropylamine. The cyclization reaction of the compound of formula XI into the compound of formula $II_c$ can be carried out in the presence of a nitrogen donor such as sodium nitrite in an acid medium such as in hydrochloric acid. The addition reaction of the compound of formula XIII onto the compound of formula XII can be carried out in a solvent such as toluene or tetrahydrofuran, preferably in the presence of a desciccating agent such as a molecular sieve, the cyclization reaction giving the compound of formula $II_d$ taking place in situ.

The halogenation reaction of the compound. of formula XIV can be carried out by the usual known methods such as in the presence of oxalyl chloride or thionyl chloride and the cyclization reaction of the compound thus obtained to give the compound of formula $II_e$ takes place in the presence of hydrazine or a hydrazine derivative while hot in an alcohol such as methanol or ethanol. The addition reaction of the acid chloride of formula XVI on the amine derivative of formula XV to obtain the compound of formula XVII can be carried out at reflux of a solvent such as pyridine. The cyclization of the product of formula XVII to obtain the product of formula $II_f$ is produced in hydrogen peroxide in the presence of aqueous sodium hydroxide at reflux of a solvent such as dioxane.

The products of formulae $I_i$ can be the products of formula $I_B$, the products of formulae $II_b$, $II_c$, $II_d$, $II_e$ and $II_f$ are products of formula $I_B$ in which $A_{1B}'$, $A_{2B}'$, $A_{3B}'$ and $A_{4B}'$ is

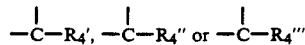

as defined above or the meanings indicated above respectively for $A_{1B}$, $A_{2B}$, $A_{3B}$ and $A_{4B}$ n in which the optional reactive functions are optionally protected by protective groups and in which at least one of $A_{1B}$, $A_{2B}$, $A_{3B}$ and $A_{4B}$ is methine carrying hydroxyl.

The products of formula $I_i$ and the products of formulae $II_b$, $II_c$, $II_d$, $II_e$ and $II_f$ particularly to give the products of formula $I_B$, can be subjected, if desired and if necessary, to one or more of the reactions above, these reactions can be in the preferred conditions carried out in the manner indicated hereafter.

The hydroxyls which either exist or derive from the oxo tautomer form of the compounds of formulae $II_b$, $II_c$, $II_d$, $II_e$ and $II_f$ or optionally the products of formula $I_i$ obtained as indicated above can be, if necessary and if desired, subjected to a complete reduction into methine. This complete reduction into methine as defined above can be carried out very preferentially after conversion of the hydroxyl into a halogen or mesylate using a reducing agent such as lithium aluminium hydride or by catalytic reduction on palladium in the presence of hydrogen.

The substitution reaction of the products of formulae $I_i$, $II_b$, $II_c$, $II_d$, $II_e$ and $II_f$ by $R_{4p}$ is subjected beforehand to a substitution reaction of the hydroxyl carried out by the preparation of the halogen derivative such as chlorine derivative prepared by treatment with a chlorinating agent such as phosphorous pentachloride or phosphorous oxychloride optionally in a solvent such as dioxane or tetrahydofuran. The substitution reaction by $R_{4p}$ defined above can be carried out by reaction with an organometal such as an organozinc of the formula $R_{4p} - Zn - Br$, if desired in the presence of a catalytic quantity of a transition metal complex such as palladium or nickel at reflux of a solvent such as tetrahydrofuran. The hydroxyl be optionally activated for example into the sulfonate such as the mesylate, tosylate or the triflate.

The conversion reaction of the oxo into a thioxo can be carried out by known methods such as using a Lawesson reagent or phosphorous pentasulfide at reflux in a solvent such as toluene or an alcohol such as ethanol. The various reactive functions which can be carried by some of the compounds defined above can, if necessary, be protected. It concerns for example hydroxyl, acyl, free, carboxy or amino and monoalkylamino which can be protected by the appropriate protective groups.

The following non-exhaustive list of examples of protective functions can be mentioned: hydroxyl groups protected by alkyl, trialkylsilyl, dihydropyran, methoxymethyl or tetrahydropyranyl, the amino groups protected by acetyl, trityl, benzyl, tert-butoxycarbonyl, phthalimido or others known in the chemistry of the peptides. The acyls such as formyl can be protected in the form of cyclic or non-cyclic ketals such as dimethyl- or diethylketal or ethylene dioxyketal and the acid functions of the products can be, if desired, amidified by a primary or secondary amine for example in methylene chloride in the presence of 1-ethyl-3-(dimethylaminopropyl) carbodiimide hydrochloride at ambient temperature. The acid functions can be protected in the form of esters formed with easily clearable esters such as benzyl or tert-butyl esters or esters known in the chemistry of the peptides.

The elimination of these protector groups is carried out under the usual known conditions, notably acid hydrolysis carried out with an acid such as hydrochloric acid, benzene sulfonic acid or p-toluene sulfonic acid, formic acid or trifluoroacetic acid. The phthalimido group is eliminated by hydrazine and a list of the different protective groups which can be used will be found, for example, in the Patent BF 2,499,995.

The products described above can, if desired, be salified by a mineral or organic acid or a mineral or organic base, particularly on the optional carboxy functions, these reactions being carried out by the usual known methods.

The products described above can, if desired, be the subject, on the optional carboxy functions, of esterification reactions which can be carried out by the usual known methods.

The optional ester functions of the products can be, if desired, saponified into an acid function by known saponification reactions, notably by acid or alkaline hydrolysis with sodium hydroxide or potassium hydroxide in an alcoholic medium such as methanol or hydrochloric or sulfuric acid.

The optional alkoxy functions such as methoxy of the products can be, if desired, converted into a hydroxyl or alcohol function by the usual known conditions by boron tribromide in a solvent such as methylene chloride, by pyridine hydrobromide or hydrochloride or by hydrobromic acid or hydrochloric acid in water or acetic acid at reflux.

The optional cyano functions of the products can be, if desired, converted into an acid function under the usual known conditions, for example by a hydrolysis carried out in an acid medium such as a sulfuric acid, glacial acetic acid and water mixture, the three compounds preferably being in equal proportions, or also in a mixture of sodium hydroxide, ethanol and water at reflux.

The optional esterified carboxy functions of the products can, if desired, be reduced to an alcohol function by known methods and notably by lithium aluminium hydride in a solvent such as tetrahydrofuran or dioxane or ethyl ether.

The optional carboxy functions of the products can, if desired, be reduced to an alcohol function by known methods and can therefore, for example, be first esterified, then converted into an alcohol function as is indicated above.

The optional optically active forms of the products of formula $I_B$ can be prepared by resolving the racemics by the usual methods.

The novel compositions having an inhibiting effect on angiotensin II are comprised of an amount of at least one compound of formula $I_B$ and its non-toxic, pharmaceutically acceptable salts sufficient to inhibit the effect of angiotension II and an inert pharmaceutical carrier. The compositions may be in the form of tablets, dragees, capsules, granules, suppositories, ointments, creams, gels, injectable solutions and aerosols.

Examples of suitable excipients or carriers are talc, lactose, starch, arabic gum, magnesium stearate, cocoa butter, aqueous or non-aqueous vehicles, fatty substances of animal or vegetable origin, paraffin derivatives, glycols, various wetting agents, emulsifiers and dispersants and preservatives.

The compositions are endowed with antagonistic properties for the angiotensin II receptor and are thus notably inhibitors of the effects of angiotensin II, particularly the vasoconstrictive effect and the trophic effect at the level of the myocytes. Some compositions of the invention also possess antagonistic properties for the endotheline receptor and are thus antagonists of the vasoconstrictive effect of endotheline. The compositions with compounds of formulae $I_B$ and I also possess the property of improving cognitive functions.

The compositions are useful in the treatment of cardiovascular illnesses presenting an alteration of vasomotricity: myocardium infract, cardiac insufficiency, renal insufficiency, angina pectoris, cerebral vascular spasm, Raynaud's disease, arterial hypertension and all illnesses following an ischemia. The compositions are also useful for the treatment of glaucoma, atherosclerosis, asthma and various types of visceral spasm, as well as neuromal protective substances and in the prevention of post-angioplastic restenoses.

They can also be used in the treatment of certain gastrointestinal and gynaecologial disorders and particularly for a relaxing effect at the level of the uterus as well as being used in the treatment of memory disorders, senile dementia and Alzheimer's disease.

The novel method of the invention for inducing an inhibiting effect of angiotensin II in warm-blooded animals, including humans, comprises administering to warm-blooded animals an amount sufficient to inhibit the effect of angiotensin II of at least one compound of formula $I_B$ and their non-toxic, pharmaceutically acceptable salts with acids and bases. The compounds may be administered orally, rectally, parenterally or topically on the skin and mucous membranes. The usual daily dose is 0.013 to 1.33 mg/kg depending on the condition treated, the specific compound used and the method of administration.

The starting compounds of formulae III, V, VI, VII, IX, X, XII, XIII, XIV, XV and XVI are commercially available or can be prepared by known methods. The compounds of formula III can be derivatives of phenylacetyl chloride.

Among the preparation examples of such compounds of formula III described in the literature are: Org. Synthesis, 1972, p. 36; Can. J. Chem., 1957, Vol. 35, p. 651.

The compounds of formula V can be nitrile-type derivatives which can be prepared as described in Synthesis, 1987, p. 514. The compounds of formula VI can be aniline derivatives and are available commercially when one of $R_2$ or $R_3$ is carbomethoxy such as methyl anthranilate, ethyl 3-aminobenzoate, which are sold for example by Aldrich.

The compounds of formula VII can be esters derived from formylacetic acid and may be prepared as described in: J. Het. Chem., Vol. 20, p. 623 to 628, 1983 and Liebigs Ann. Chem., Vol. 697, p. 62 to 68, 1966.

The compounds of formula IX can be particularly ortho halo aniline derivatives which can be prepared as described in Ann. Chem., 1962 Vol. 52, p. 727. The compounds of formula X can be particularly acetylene derivatives which are prepared as described in J. Am. Chem. Soc., 1937, Vol. 59, p. 1490.

Among the compounds of formula XII which can be found commercially are for example methyl 3,4-diaminobenzoate which is marketed for example by LANCASTER. The compounds of formula XII described in the literature may be found in Org. Synth. 1943, 501.

The compounds of formula XIII can be glyoxylic acid derivatives which can be prepared by the process described in J. Org. Chem., 1979, Vol. 44, 1613. The compounds of formula XIV can be phthalic acid derivatives which are prepared as described in J. Org. Chem. 1963, Vol. 28, p. 582 and J. Chem. Soc. 1952, p. 553.

The compounds of formula XV can be cyanoaniline derivatives which can be found commercially, for example 2-aminobenzonitrile marketed by Aldrich, or 5-chloro-2-cyanoaniline marketed by Bayer. The compounds of formula XVI can be acyl chloride derivatives which can be prepared as described in Org. Synth. Coll., Vol. III, p. 190.

Also, certain intermediate products can be found commercially such as chlorinated derivatives like 4-chloro-2-phenylquinazoline supplied by ALDRICH which can be prepared as described in J- Org. Chem., Vol. 37, p- 1681 (1972). The compound 4-chloro-2-phenylquinazoline enables the products of formula I derived from 2-phenylquinazoline to be prepared into which, by the intermediary for example of an organometallic compound such as $R_4$ - Zn - Br, $R_4$ is defined as above can be introduced by substitution on the chlorine under the known conditions.

Also an object of the invention is, as new intermediate products necessary for the preparation of products of formula I are the compounds of formulae VIII, II$_b$, II$_c$, II$_d$, II$_e$ and II$_f$.

Particularly useful in the inhibition of the effects of angiotensin II are the products of the formula

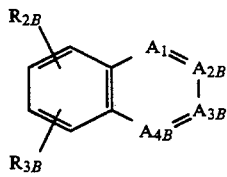

$F_B$ in which: $R_{2B}$ and $R_{3B}$ are individually selected from the group consisting of:

a) hydrogen, halogen, hydroxyl, mercapto, cyano, nitro, sulfo, formyl, benzoyl, acyl of up to 12 carbon atoms, free, salified and esterified carboxy, cycloalkyl of 3 to 7 carbon atoms, acyloxy of up to 12 carbon atoms, b) alkyl, alkenyl, alkynyl, alkoxy and alkylthio of up to 6 carbon atoms and optionally substituted, c) aryl, aralkyl, aralkenyl, aryloxy and arylthio with 1 to 6 alkyl and alkenyl carbon atoms, the aryl is a monocycle of 5 or 6 ring members or condensed rings of 8 to 10 ring members optionally containing one or more heteroatoms chosen from oxygen, nitrogen and sulfur and optionally substituted,

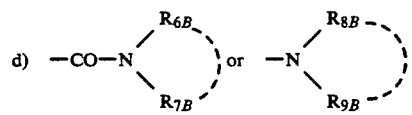

in which: either $R_{6B}$ and $R_{7B}$ or $R_{8B}$ and $R_{9B}$ are individually selected from the group consisting of hydrogen, alkyl and alkenyl of up to 6 carbon atoms and optionally substituted by at least one halogen and hydroxyl, alkyl and alkenyl of 2 to 6 carbon atoms substituted by alkoxy of 1 to 6 carbon atoms, aryl or aralkyl with 1 to 6 alkyl carbon atoms, the aryl is mono-cyclic of 5 or 6 ring members or condensed rings of 8 to 10 ring members optionally containing one or more heteroatoms chosen from oxygen, nitrogen and sulfur and optionally substituted by at least one member of the group consisting of halogen, hyroxyl, cyano, trifluoromethyl, nitro, alkyl, alkenyl, alkoxy, alkylthio and acyl of up to 6 carbon atoms, free, salified and esterified carboxy $-(CH_2)_{m1}-S(O)_{m2}-X-R_{14}$, $m_1$ is an integer from 0 to 4, $m_2$ is an integer from 0 to 2, and either $-X-R_{14}$ is $-NH_2$ or X is a member of the group consisting of $-NH-$, $-NH-CO-$, $NH-CO-NH-$ and a single bond and $R_{14}$ is alkyl, alkenyl or aryl optionally substituted, or $R_{6B}$ and $R_{7B}$ and $R_{8B}$ and $R_{9B}$ form respectively with the nitrogen atom to which they are attached a monocycle of 5 or 6 ring members or condensed rings of 8 to 10 ring members optionally containing one or more heteroatoms chosen from oxygen, nitrogen and sulfur and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified and esterified carboxy, or $R_{8B}$ and $R_{9B}$ individually are acyl of a carboxylic acid of up to 6 carbon atoms, e) $-(CH_2)_{m1}-S(O)_{m2}-X-R_{14}$ as defined above, $A_{1B}$, $A_{2B}$, $A_{3B}$ and $A_{4B}$ are such that one is nitrogen, another is nitrogen or methine substituted by $R_{4b}$, another is methine substituted by $R_{4c}$, and the last one is methine substituted by optionally substituted benzyl, $R_{4b}$ and $R_{4c}$ are chosen from the values of $R_{4B}$, such that $R_{4B}$ is selected from the group consisting of a) hydrogen, hydroxyl, cyano, benzoyl, acyl of 12 carbon atoms, free, salified and esterified carboxy, cycloalkyl of 3 to 7 carbon atoms, b) alkyl, alkenyl, alkynyl, alkoxy and alkylthio of up to 6 carbon atoms and optionally substituted, the said products of formula $F_B$ being in all possible racemic, enantiomeric and diastereoisomeric isomer forms, as well as their addition salts with mineral and organic acids or mineral and organic bases. The compounds of formula $F_B$ are useful for the treatment of arterial hypertension, cardiac insufficiencies, renal insufficiencies and in the prevention of post-angioplastic restenoses, or for the treatment of certain gastrointestinal or gynaecological disorders.

More preferred for the inhibition of the effects of angiotensin II is the use of the products of the formula

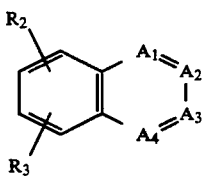

F in which:

$R_2$ and $R_3$ are individually selected from the group consisting of a) hydrogen, halogen, hydroxyl, mercapto, cyano, nitro, sulfo, formyl, benzoyl, acyl of up to 12 carbon atoms, free, salified and esterified carboxy, cycloalkyl of 3 to 7 carbon atoms, b) alkyl, alkenyl, alkynyl, alkoxy and alkylthio of up to 6 carbon atoms and optionally substituted, c) aryl, aralkyl, aralkenyl, aryloxy and arylthio with 1 to 6 alkyl and alkenyl carbon atoms, the aryl being monocycle of 5 or 6 ring members or condensed rings of 8 to 10 ring members optionally containing one or more heteroatoms chosen from oxygen, nitrogen and sulfur and optionally substituted,

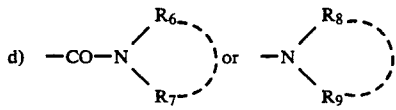

in which:

either $R_6$ and $R_7$ or $R_8$ and $R_9$ individually are selected from the group consisting of hydrogen, alkyl and alkenyl of up to 6 carbon atoms and optionally substituted by at least one halogen or hydroxyl, alkyl and alkenyl of 2 to 6 carbon atoms substituted by alkoxy of 1 to 6 carbon atoms, aryl and aralkyl with 1 to 6 alkyl carbon atoms, the aryl being a monocycle of 5 or 6 ring members or condensed rings of 8 to 10 ring members optionally containing one or more heteroatoms chosen from oxygen, nitrogen and sulfur and optionally substituted by at least one member selected from the group consisting of halogen, hydroxyl, cyano, trifluoromethyl, nitro, alkyl, alkenyl, alkoxy, alkylthio and acyl of up to 6 carbon atoms, free, salified and esterified carboxy, or $R_6$ and $R_7$ or $R_8$ and $R_9$ form respectively with the nitrogen atom to which they are attached a monocycle of 5 or 6 ring members or condensed rings of 8 to 10 ring members optionally containing one or more heteroatoms chosen from oxygen, nitrogen, and sulfur and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified and esterified carboxy, or $R_8$ and $R_9$ individually are an acyl of a carboxylic acid of up to 6 carbon atoms, $A_1$, $A_2$, $A_3$ and $A_4$ are such that one is nitrogen, another is nitrogen or methine substituted by $R_{4b}$, another is methine substituted by $R_{4c}$, and the last one is methine substituted by an optionally substituted benzyl, $R_{4b}$ and $R_{4c}$ individually are chosen from the values of $R_4$, $R_4$ is selected from the group consisting of a) hydrogen, hydroxyl, cyano, benzoyl, acyl of up to 12 carbon atoms, free, salified or esterified carboxy, cycloalkyl of 3 to 7 carbon atoms, b) alkyl, alkenyl, alkynyl, alkoxy and alkylthio of up to 6 carbon atoms and optionally substituted, the said products of formula F being in all possible racemic, enantiomeric and diastereoisomeric isomer forms, as well as their addition salts with mineral and organic acids or mineral and organic bases.

The compounds of formula F are useful for the treatment of arterial hypertension, cardiac insufficiencies, renal insufficiencies and in the prevention of post-angioplastic restenoses, or for the treatment of certain gastrointestinal or gynaecological disorders and especially for the treatment of arterial hypertension, cardiac insufficiencies, renal insufficiencies and in the prevention of post-angioplastic restenoses.

Another preferred group for the inhibition of effects of angiotension II is the use of products of the formula

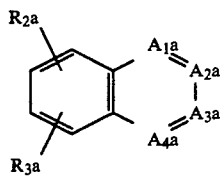

in which:

$R_{2a}$ and $R_{3a}$ individually are chosen from the group consisting of hydrogen, halogen, hydroxy, mercapto, cyano, nitro, formyl, benzoyl, acyl of up to 6 carbon atoms, carboxy, free, salified or esterified by alkyl of 1 to 4 carbon atoms, alkyl, alkoxy and alkylthio of up to 6 carbon atoms, phenyl, naphthyl, benzyl and phenylthio, all optionally substituted by at least one member of the group consisting of halogen, hydroxyl, alkoxy, of 1 to 4 carbon atoms, trifluoromethyl, cyano, acyl, free, salified and esterified carboxy, tetrazole and isoxazole, amino, mono- or dialkylamino, carbamoyl, pyrrolyl, morpholino, piperazinyl, pyrrolylmethyl, morpholinomethyl, piperazinylmethyl, pyrrolylcarbonyl, morpholinocarbonyl, piperazinylcarbonyl, all the piperazinyls optionally substituted on the second nitrogen atom by alkyl or phenyl optionally substituted by at least one member of the group consisting of halogen, hydroxyl, nitro, alkyl, alkoxy and acyl of 1 to 4 carbon atoms, trifluoromethyl, cyano, free, salified and esterified carboxy, tetrazole and isoxazole, $A_{1a}$, $A_{2a}$, $A_{3a}$ and $A_{4a}$ are such that: one is a nitrogen, one is nitrogen or methine substituted by $R_{4a}$, another is methine substituted by $R_{4a}$, and the last one is methine substituted by optionally substituted benzyl such that $R_{4a}$ is selected from the group consisting of hydrogen, hydroxyl, cyano, carboxyl, free, salified and esterified by alkyl of 1 to 4 carbon atoms, alkyl, alkenyl, alkoxy, acyl and alkylthio of up to 7 carbon atoms, all optionally substituted by at least one member of the group consisting of halogen, hydroxy, nitro, alkyl, alkoxy, and acyl of 1 to 4 carbon atoms, trifluoromethyl, cyano, carboxy, free, salified and esterified by alkyl of 1 to 4 carbon atoms, tetrazole and isoxazole, the said products of formula $F_a$ being in all possible racemic, enantiomeric and diastereoisomeric isomer forms, as well as their addition salts with mineral and organic acids or mineral and organic bases.

Among the most preferred products of formula I are those of the formulae indicated below in which $R_2$ and $R_3$ have the meanings indicated above, n-bu is n-butyl and R', R" and R''' are optional substituents which can be carried by phenyl these substituents being able to take the values defined above:

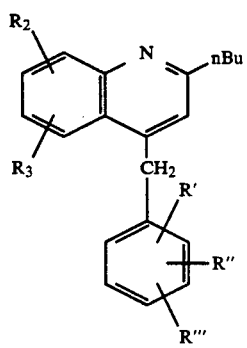

-continued

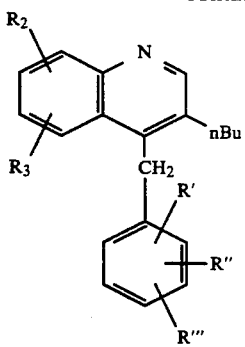

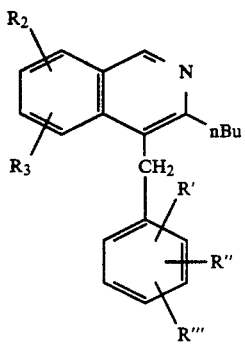

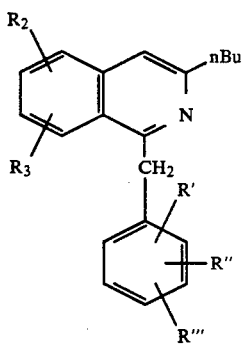

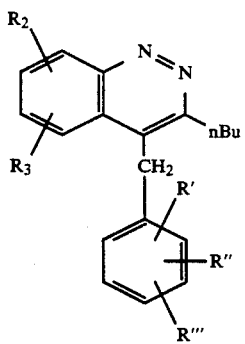

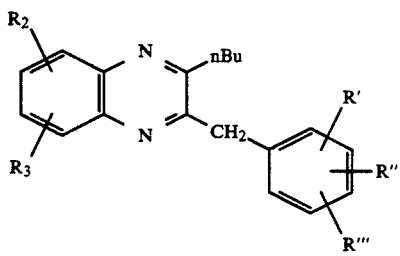

-continued

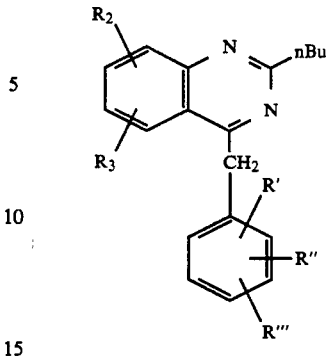

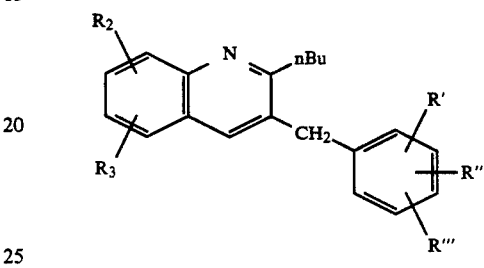

In the following examples, there are described several preferred embodiments to illustrate the invention. However, it is to be understood that the invention is not intended to be limited to the specific embodiments.

EXAMPLE 1

(4-[(3-butyl-4-quinolinyl)-methyl]-benzonitrile

STEP A: Diethyl 2-butyl-3-oxo-butanedioate 13.55 ml of diethyl oxalate were added to a suspension of sodium ethylate (prepared by stirring for one hour at 40° C. of 2.3 g of sodium and 150 ml of ethanol and then evaporation of the solvent) in 100 ml of ether. The mixture was refluxed for 15 minutes and then cooled down slightly. 50 ml of ethyl caproate were added and the mixture was stirred for 3 hours at reflux and for 16 hours at 30° C. to 35° C. 50 ml of water were added and the aqueous phase was separated by decanting, washed twice with ether and acidified with 2N hydrochloric acid. Extraction was done 3 times with ether and the combined organic phases were washed with water, then with a saturated solution of sodium chloride, dried and evaporated to dryness to obtain 9.5 g which was used as is for the following step.

STEP B: Diethyl 2-butyl-3-(phenylamino)-2-butenedioate

A mixture of 1 g of aniline and 2.65 g of the product of Step A and 150 mg of siliporite ® NK10 was stirred for 3 days at 75° C. and the reaction mixture was cooled and chromatographed on silica eluant: hexane - ethyl acetate (9–1) to obtain 1.55 g of the expected product.

| IR Spectrum (in CHCl$_3$): | |
|---|---|
| =C—NH | 3260 cm$^{-1}$ |
| C=O | 1733–1656 cm$^{-1}$ |
| C=C | 1610 cm$^{-1}$ (shoulder) |
| + | 1596 cm$^{-1}$ |
| Aromatics | 1584 cm$^{-1}$ |
| | 1500 cm$^{-1}$ |

STEP C: Ethyl 3-butyl-4-hydroxy-2-quinolinecarboxylate and ethyl 3-butyl-1,4-dihydro-4-oxo-2-quinolinecarboxylate A mixture of 2.5 g of the product of Step B and 30 ml of diphenylether was heated for 30 minutes in a bath at 250° C. The mixture was allowed to return to ambient temperature, separated and washed with pentane to obtain 1.82 g of the desired product.

| IR Spectrum (in CHCl$_3$): | |
|---|---|
| =C—NH | 3425-3383 cm$^{-1}$ |
| C=O | 1746-1706 cm$^{-1}$ (F) |
| other C=O | 1624 cm$^{-1}$ |
| C=C | 1605 cm$^{-1}$ |
| + | 1585 cm$^{-1}$ |
| Aromatics | 1572 cm$^{-1}$ |
| | 1532 cm$^{-1}$ |

STEP D: 3-butyl-1,4-dihydro-4-oxo-2-quinolinecarboxylic acid 1.8 g of the ester of Step C was heated for one hour at 60° C. with 25 ml of a N sodium hydroxide solution and the mixture was cooled and acidified with N hydrochloric acid, followed by filtering, washing with water and drying at 60° C. under reduced pressure to obtain 1.58 g of the desired product.

| NMR 60 MHz (D.M.S.O.) ppm: | |
|---|---|
| $\underline{CH_3}$—CH$_2$—CH$_2$—CH$_2$— | 0.89 (t) |
| C—$\underline{C}$—$\underline{C}$—C— | 1.39 (m) |
| C—$\underline{C}$—$\underline{C}$—$\underline{C}$— | 2.78 |
| H$_6$ and H$_7$ | 7.30 (t)-7.63 (t) |
| H$_5$ and H$_8$ | 7.80 (d)-8.08 (d) |
| Mobile | 11.64 |

STEP E: 3-butyl-4-(1H)-quinolone

A mixture of 1.55 g of the product of Step D and 10 ml of diphenyl ether was heated for 30 minutes at 250° C. and then cooled and filtered. The filtrate was washed with pentane and dried under reduced pressure to obtain 1.17 g of residue which was dissolved in 80 ml of ethanol and treated for 15 minutes at reflux in the presence of activated charcoal. Filtration was carried out on hyflosupercel and the ethanol was evaporated to dryness. The residue was taken up in pentane, filtered, washed with pentane and dried at 50° C. under reduced pressure to obtain 971 mg of the desired product.

| IR Spectrum (in CHCl$_3$): | |
|---|---|
| (2 form mixture: enol and keto) | |
| =C—NH | 3440 cm$^{-1}$ + general absorption |
| C=O | 1632 cm$^{-1}$ |
| C=C | 1590 cm$^{-1}$ |
| + | 1570 cm$^{-1}$ (shoulder) |
| Aromatics | 1558 cm$^{-1}$ |
| | 1524 cm$^{-1}$ 1506 cm$^{-1}$ |

STEP F: 3-butyl-4-chloro quinoline

A mixture of 515 mg of the product of Step E and 0.6 ml of phosphorous oxychloride was heated for 2 hours at 120° C. and the mixture was cooled. 10 ml of water were added and the solution was alkalized to pH 9 with concentrated ammonium hydroxide. Extraction was carried out twice with methylene chloride and the extracts were washed with a saturated solution of sodium chloride, dried and evaporated to dryness. The residue was dissolved in 30 ml of ethanol and treated for 15 minutes at reflux in the presence of activated charcoal, followed by filtering on hyflosupercel to obtain 511 mg of the desired product.

| NMR CDCl$_3$ (250 MHz): | |
|---|---|
| $\underline{CH_3}$—CH$_2$—CH$_2$—CH$_2$—C— | 0.98 (t) |
| CH$_3$—$\underline{CH_2}$—CH$_2$—CH$_2$—C— | 1.45 (m) |
| CH$_3$—CH$_2$—$\underline{CH_2}$—CH$_2$—C— | 1.68 (m) |
| CH$_3$—CH$_2$—CH$_2$—$\underline{CH_2}$—C— | 2.96 (m) |
| | 7.63 (dt) |
| Aromatic H's | 7.72 (dt) |
| | 8.10 (dd) 8.25 (dd) |
| H pyridine nucleus | 8.74 (s) |

STEP G: 4-[(3-butyl-4-quinolinyl)-methyl-]-benzonitrile 14 ml of a 0.38M solution of 4-bromomethyl benzonitrile zinc in tetrahydrofuran (prepared by Knochel, J. Org. Chem., (1988) Vol. 53, pages 5789 to 5791) were added to a stirred mixture of 0.720 g of 4-chloro-3-butyl quinoline of Step F with 0.8 ml of tetrahydrofuran and 0.663 g of tetrakis triphenylphosphine palladium. The mixture was stirred for 4 hours at 60° C., then for 16 hours at ambient temperature. The mixture was hydrolyzed with 100 ml of 0.1N hydrochloric acid and then extracted with ethyl acetate. The extracts were washed with a saturated solution of sodium chloride, dried and evaporated to dryness. The residue was chromatographed on silica (eluant: hexane - ethyl acetate (7-3)) to obtain 0,445 g of the desired product.

| IR Spectrum (CHCl$_3$): | |
|---|---|
| C≡N | 2232 cm$^{-1}$ |
| Aromatics | 1609-1573-1506 cm$^{-1}$ |

EXAMPLE 2

4-[(3-butyl-4-quinolinyl)-methyl]-benzoic acid 0.340 g of the compound of Example I and 2 ml of ethanol and 5 ml of 2N sodium hydroxide solution were stirred for 15 hours at 80° C. and the ethanol was evaporated- The residue was taken up in water and acidified to pH 4 with acetic acid, followed by filtering, washing with water and drying to 50° C. under reduced pressure to obtain 345 mg of the desired product. The product was dissolved in 50 ml of an ethanol - methylene chloride mixture (1-1) and treated at reflux with activated charcoal. Filtration was carried out on hyflosupercel and the filtrate was evaported until almost dry. The residue was taken up in 50 ml of isopropanol to obtain 205 mg of the expected product melting at about 233° C.

| Analysis: | | | | | | |
|---|---|---|---|---|---|---|
| C$_{21}$H$_{21}$NO$_2$; molecular weight = 319.41 | | | | | | |
| Calculated: | % C | 78.97 | % H | 6.62 | % N | 4.38 |
| Found: | | 79.0 | | 6.8 | | 4.2 |

| IR Spectrum (Nujol) | |
|---|---|
| very associated OH/NH absorption | |
| C=O | 1690 cm$^{-1}$ |
| Aromatics | 1608 cm$^{-1}$ |
| + | 1576 cm$^{-1}$ |
| Heterocycle | 1508 cm$^{-1}$ |

EXAMPLE 3

4-[(2-butyl-4-quinolinyl)-methyl]-benzonitrile STEP A; Ethyl 3-oxo-heptanoate 70.8 g of ethyl carbonate in solution in 50 ml of ether were added to a suspension of 27.3 g of sodium hydride at 50% in oil (washed beforehand in heptane) and 250 ml of ether and the mixture was stirred for 10 minutes. 30 g of hexanone were added over 30 minutes and the mixture was refluxed for 2 hours. 35 ml of ether with 12 ml of ethanol were added and the mixture was stirred for 16 hours at ambient temperature. After cooling to 0° C., a solution of 36 ml of acetic acid in 300 ml of water, then 12 ml of a saturated sodium bicarbonate solution were added, and the pH was 7. Extraction was carried out with ether and the extracts were washed with water, dried and evaporated to dryness. After distillation to 70° C. under a reduced pressure of 7 mbar, 32.5 g of the desired product were obtained.

| NMR Spectrum: | |
|---|---|
| $\underline{CH_3}$—$CH_2$— | 0.91 ppm |
| the central $CH_2$'s | 1.39 |
| | 1.59 |
| $CH_2$—C<br>‖<br>O | 2.55 (t) ppm |
| $CO_2Et$ | 1.28 (t) ppm |
| | 1.59 (q) ppm |
| C—$CH_2$—C<br>‖       ‖<br>O       O | 3.44 (o) ppm |

STEP B: Ethyl 3-(phenylamino) heptanoate

Using the procedure of Step B of Example 1, 45 g of the product of Step A were reacted to obtain after chromatography on silica (eluant: hexane - ethyl acetate (95-5)), 28.7 g of the expected product.

| IR Spectrum (CHCl$_3$): | |
|---|---|
| NH | 3260 cm$^{-1}$ |
| C=O | 1648 cm$^{-1}$ |
| C=C | 1612 cm$^{-1}$ |
| + | 1594 cm$^{-1}$ |
| Aromatic | 1588 cm$^{-1}$ |

STEP c: 2-butyl-4-quinolone

Using the procedure of Step C of Example 1, 28.7 g of the compound of Step B were reacted to obtain 16.95 g of the desired product melting at 140° C.

| IR Spectrum (CHCl$_3$): | |
|---|---|
| =C—NH | 3428 cm$^{-1}$ + strong general absorption |
| C=O + | 1636 cm$^{-1}$ |
| C=C + | 1596 cm$^{-1}$ |
| C=N + | 1547 cm$^{-1}$ |

| IR Spectrum (CHCl$_3$): | |
|---|---|
| Aromatics | 1502 cm$^{-1}$ |

STEP D: 2-butyl-4-chloro quinoline

Using the procedure of Step F of Example 1, 4 of the compound of Step C were reacted to obtain 3.89 g of the desired product.

| NMR CDCl$_3$ | |
|---|---|
| $\underline{CH_3}$—$CH_2$—$CH_2$—$CH_2$ | 0.97 (t) |
| $CH_3$—$\underline{CH_2}$—$CH_2$—$CH_2$ | 1.45 (m) |
| $CH_3$—$CH_2$—$\underline{CH_2}$—$CH_2$ | 1.72 (m) |
| $CH_3$—$CH_2$—$CH_2$—$\underline{CH_2}$ | 2.95 (m) |
| | 7.41 (dt) |
| Aromatic H's | 7.74 (dt) |
| | 8.06 (dd) |
| | 8.19 (dd) |
| H pyridine | 7.41 (s) |

STEP E: 4-[(2-butyl-4-quinolinyl)-methyl]-benzonitrile

Using the procedure of Step G of Example 1, 0.614 g of 4-chloro-2-butyl quinoline of Step D, 0.8 ml of tetrahydrofuran, 0.323 g of tetrakis triphenylphosphine palladium and 10 ml of a 0.5 M 4-bromomethyl benzonitrile zinc solution in tetrahydrofuran were reacted to obtain after chromatography on silica (eluant: hexane - ethyl acetate (8-2)) 0.781 g of the desired product.

| IR Spectrum (CHCl$_3$): | |
|---|---|
| C≡N | 2230 cm$^{-1}$ |
| Aromatic | 1600 cm$^{-1}$ |
| + | 1580 cm$^{-1}$ |
| Heterocycle | 1508 cm$^{-1}$ |

EXAMPLE 4

4-[(2-butyl-4-quinolinyl)-methyl]-benzoic acid

Using the procedure of Example 2, 0.750 g of the product of Example 3 and 2.5 ml of water and 2.5 ml of sodium hydroxide were reacted to obtain 205 mg of the desired product which after cry-stallization melted at 158° C.

Analysis:
$C_{21}H_{21}NO_2$; molecular weight = 319.41

| | | | | | | |
|---|---|---|---|---|---|---|
| Calculated: | % C | 78.97 | % H | 6.62 | % N | 4.38 |
| Found: | | 79.2 | | 6.7 | | 4.3 |

| IR Spectrum (Nujol): | |
|---|---|
| very associated OH/NH absorption | |
| C=O | 1629 cm$^{-1}$ |
| Aromatics | 1608 cm$^{-1}$ |
| + | 1568 cm$^{-1}$ |
| Heterocycle | 1510 cm$^{-1}$ |

EXAMPLE 5

4-[(3-butyl-4-cinnolinyl)-methyl]-benzonitrile

STEP A: 2-(1-hexynyl) benzeneamine 32 mg of copper iodide, 140 mg of bistriphenyl phosphine palladium chloride and then 2.3 ml of 1-hexyne were added to a solution of 4.4 g of 2-iodo aniline in 100 ml of triethylamine. The mixture was stirred for 15 hours at ambient temperature, followed by evaporating to dryness and taking up in ether. The insoluble part was filtered off, washed with ether and the ethereal fractions were evaporated to dryness. The residue was chromatographed on silica (eluant: hexane - ethyl acetate (9-1)) to obtain 3.27 g of the desired product.

| IR Spectrum: | |
|---|---|
| $C_6H_4$—$NH_2$ | 3486-3390 cm$^{-1}$ |
| $NH_2$ def | 1613 cm$^{-1}$ |
| + | 1570 cm$^{-1}$ |
| Aromatic | 1493 cm$^{-1}$ |

STEP B: 3-butyl-4-hydroxy cinnoline

A solution of 2 g of sodium nitrate in 60 ml of water was added at 0° C. to a suspension at 0° C. of 3.2 g of the product of Step A in 100 ml of concentrated hydrochloric acid. The mixture was stirred for 90 minutes at 0° C., then for one hour at 100° C. The reaction medium was poured into 100 ml of ice-cooled water, followed by separating and washing with ice-cooled water. The moist product was taken up in 100 ml of water and alkalized with concentrated ammonium hydroxide. After separating, the residue was washed with water and dried at 70° C. under reduced pressure to obtain 1.47 g of the expected product melting at 180° C.

| IR Spectrum (Nujol): | |
|---|---|
| Absorption OH/NH region | |
| C=C | 1636 cm$^{-1}$ |
| + | 1604 cm$^{-1}$ (shoulder) |
| Aromatic | 1580 cm$^{-1}$ |
| | 1578 cm$^{-1}$ |
| | 1498 cm$^{-1}$ |

STEP C: 3-butyl-4-chloro cinnoline

Using the procedure of Step F of Example 1, 1.2 g of the product of Step B and 10 ml of phosphorous oxychloride were reacted to obtain after chromatography on silica (eluant: hexane - ethyl acetate (6-4)), 1.16 g of the desired product melting at 50° C.

| IR Spectrum (CHCl$_3$): | |
|---|---|
| C=C | 1616 cm$^{-1}$ |
| + | |
| Aromatic | 1558 cm$^{-1}$ |

STEP D: 4-[(3-butyl-4-cinnolinyl)-methyl]-benzonitrile 100 mg of nickel diphenyl phosphino propane chloride were added to a solution of 0.87 g of 3-butyl-4-chloro cinnoline of Step C and 30 ml of tetrahydrofuran and the mixture was refluxed. 10 ml of a 0.5 M solution in tetrahydrofuran of 4-bromomethyl benzonitrile zinc (prepared as Knochel, J. Org. Chem., (1988), Vol. 53. p. 5789 to 5791) were added, followed by stirring for one hour at 50° C., then pouring into ice-cooled water. The solution was alkalized by the addition of ammonium hydroxide, concentrated and extracted with ethyl acetate. The extracts were washed with water, dried and evaporated to dryness. The residue was chromatographed on silica (eluant: ethyl acetate - hexane (1-1)) to obtain 680 mg of the desired product.

| IR Spectrum (CHCl$_3$): | |
|---|---|
| C≡N | 2232 cm$^{-1}$ |
| C=C | 1609 cm$^{-1}$ |
| + | 1568 cm$^{-1}$ |
| Aromatic | 1538 cm$^{-1}$ |
| | 1508 cm$^{-1}$ |
| | 1493 cm$^{-1}$ |

4-[(3-butyl-4-cinnolinyl)-methyl]-benzoic acid hydrochloride

A solution of 0.38 g of the product of Example 5 and 1.3 ml of 5N sodium hydroxide solution and 10 ml of ethanol was stirred at reflux for 6 hours and the solution was poured into water and acidified by the addition of sodium hydrogen phosphate and separated. The residue was washed with water and dried at 60° C. under reduced pressure to obtain 380 mg of the expected product melting at 220° C.

Preparation of the hydrochloride 0.09 ml of concentrated hydrochloric acid were added to a solution of 320 mg of the above base in 20 ml of ethyl acetate and 10 ml of acetonitrile. The mixture was stirred for one hour at ambient temperature, followed by separating, washing with ethyl acetate and drying at 40° C. under reduced pressure to obtain 190 mg of the desired product melting at 212° C.

| Analysis: | | | | | | | | |
|---|---|---|---|---|---|---|---|---|
| $C_{20}H_{21}N_2O_2Cl$; molecular weight = 356.85 | | | | | | | | |
| Calculated: | % C | 67.32 | % H | 5.93 | % N | 7.85 | % Cl | 9.93 |
| Found: | | 67.5 | | 6.0 | | 8.0 | | 10.0 |

| IR Spectrum (Nujol): | |
|---|---|
| Absence C≡N | |
| General absorption OH/NH | |
| C=O | 1698 cm$^{-1}$ |
| C=C | 1612 cm$^{-1}$ |
| + | 1570 cm$^{-1}$ |
| Aromatics | 1494 cm$^{-1}$ |

EXAMPLE 7

Methyl 4-[(3-butyl-1-isoquinolinyl)-methyl]-benzoate

STEP A: Methyl 4-(bromomethy)-benzoate

Diazomethane was added slowly to a suspension of 10 g of 4-(bromomethyl)-benzoic acid in 50 ml of methylene chloride until a persistent yellow coloring of the medium was obtained and excess diazomethane was destroyed by the addition of acetic acid. The mixture was evaporated to dryness and the residue was washed with water and dried under reduced pressure at ambient temperature to obtain 9.25 g of the desired product melting at 54° C.

STEP B: Methyl 4-cyanomethyl benzoate.

3.4 g of potassium cyanide were added to a solution of 4 g of the product of Step A in 50 ml of methanol and the mixture was stirred for 4 hours at reflux. The reaction medium was poured into water and extracted with ethyl acetate. The extracts were washed with water, dried and evaporated to dryness. The residue was chromatographed on silica (eluant: hexane - ethyl acetate (7-3)) to obtain 2.4 g of the expected product melting at 154° C.

| IR Spectrum (CHCl₃): | |
|---|---|
| C≡N | 2255 cm⁻¹ |
| C=O | 1720 cm⁻¹ |
| | 1616 cm⁻¹ |
| Aromatics | 1580 cm⁻¹ |
| | 1514 cm⁻¹ |

STEP C: 1-phenyl-2-hexanone 100 ml of n-tetrabutyl tin, then 120 mg of [benzyl (chloro) bis(triphenyl phosphine)]palladium were added to a solution of 40 ml of phenyl acetyl chloride in 500 ml of tetrahydrofuran. The mixture was stirred for 15 hours at reflux, filtered on clarcel and evaporated to dryness. The residue was distilled at 65° C. to 68° C. under 0.5 mm of mercury and the main fraction was chromatographed on silica (eluant: hexane - ethyl acetate (9-1)) to obtain 27.5 g of the desired product.

| IR Spectrum (CHCl₃): | |
|---|---|
| C≡N | 1711 cm⁻¹ |
| C=O | 1600 cm⁻¹ |
| + | 1584 cm⁻¹ |
| Aromatics | 1496 cm⁻¹ |

STEP D: Methyl 4-[(3-butyl-1-isoquinolinyl)-methyl]-benzoate 0.3 ml of stannic chloride were added to a solution of 400 mg of 1-phenyl-2-hexanone of Step B with 400 mg of methyl 4-cyano methyl benzoate of Step A and 10 ml of phosphore oxychloride and the mixture was stirred for 2 hours at reflux. The reaction medium was poured into water and alkalized by the addition of concentrated ammonium hydroxide and extracted with ethyl acetate. The extracts were washed with water, dried and evaporated to dryness. The residue was chromatographed on silica (eluant: hexane - ethyl acetate (7-3)) to obtain 470 mg of the desired product.

| IR Spectrum (CHCl₃): | |
|---|---|
| O<br>‖<br>C—OMe | 1717 cm⁻¹<br>1437 cm⁻¹ |
| Aromatic<br>+<br>Heterocycle | 1626 cm⁻¹<br>1611 cm⁻¹<br>1592 cm⁻¹<br>1566 cm⁻¹<br>1510 cm⁻¹<br>1495 cm⁻¹ |

EXAMPLE 8

4- [(3-butyl-1-isoquinolinyl) -methyl]-benzoic acid

Using the procedure of Example 2, 550 mg of the compound of Example 7 were reacted to obtain 500 mg of product melting at 110° C., which is crystallized from 10 ml of an acetonitrile - isopropyl ether mixture (1-1) to obtain 240 mg of the expected product melting at 112° C.

Analysis:
C₂₁H₂₁NO₂; molecular weight = 319.41
Calculated: % C 78.97 % H 6.63 % N 4.38
Found: 78.8 6.5 4.3

| IR Spectrum (Nujol) | |
|---|---|
| C=O | 1687 cm⁻¹ |
| | 1627 cm⁻¹ |
| | 1609 cm⁻¹ |
| C=C | 1596 cm⁻¹ |
| + | 1575 cm⁻¹ |
| Aromatics | 1564 cm⁻¹ |
| | 1508 cm⁻¹ |
| | 1496 cm⁻¹ |

EXAMPLE 9

Methyl 4-[(3-butyl-1-ethylthio-4-isoquinolinyl)-methyl]-benzoate

STEP A: 4-(3-oxo-2-phenyl-heptyl)-benzonitrile 240 mg of sodium hydride as a suspension at 50% in oil were added to a solution of 0.81 g of 1-phenyl-2-hexanone of Step A of Example 7 in 20 ml of tetrahydrofuran and the mixture was stirred for 90 minutes at 40° C. Then, a solution of 900 mg of 4-(bromo-methyl)-benzonitrile in 10 ml of tetrahydrofuran was added and after stirring for 2 hours at ambient temperature, the reaction mixture was poured into water. Extraction was carried out with ethyl acetate and the extracts were washed with water, dried, and evaporated to dryness. The residue was chromatographed on silica (eluant: methylene chloride - hexane (1-1)) to obtain 1.1 g of the desired product melting at 70° C.

| IR Spectrum (CHCl₃): | |
|---|---|
| C≡N | 2230 cm⁻¹ |
| C=O | 1712 cm⁻¹ |
| C₆H₅—C | 1494 cm⁻¹ |
| Other aromatic | 1609-1505 cm⁻¹ |

STEP B: 4-(3-oxo-2-phenyl-heptyl)-benzoic acid 3.5 g of product of Step A with 20 ml of N sodium hydroxide solution and 50 ml of ethanol were stirred for 15 hours at reflux and the reaction medium was poured into ice-cooled water and acidified with concentrated hydrochloric acid. After separating, the residue was washed with water and dried. The crude product was impasted in 100 ml of isopropyl ether to obtain 3.27 g of the desired compound melting at 140° C.

| IR Spectrum (Nujol): | |
|---|---|
| Absence of C≡N | |
| C=O | 1708-1677 cm⁻¹ |
| Aromatic | 1610-1575-1494 cm⁻¹ |

STEP C: Methyl 4- (3 -oxo-2 -phenyl-heptyl) -benzoate

Using the procedure of Step A of preparation B of Example 7, 3.27 g of the product of Step B were reacted to obtain 3.36 g of the expected product melting at 58° C.

| IR Spectrum (CHCl₃): | |
|---|---|
| Absence of acid | |
| C=O | 1714 cm⁻¹ |
| Aromatic | 1611 cm⁻¹ |

| IR Spectrum (CHCl₃): | |
|---|---|
| | 1600 cm⁻¹ (shoulder) |
| | 1586 cm⁻¹ 1575 cm⁻¹ 1564 cm⁻¹ |
| | 1510 cm⁻¹ 1493 cm⁻¹ |
| H₃ ester | 1437 cm⁻¹ |

STEP D: Methyl 4-[(3-butyl-1-ethylthio-4-isoquinolinyl)-methyl]-benzoate 0.4 ml of ethyl thiocyanate and 0.45 ml of stannic chloride were added to a solution of 1 g of methyl 4-(3-oxo-2-phenyl-heptyl) benzoate of Step C in 20 ml of phosphorous oxychloride and the mixture was stirred for 10 hours at reflux, then poured into ice-cooled water. The mixture was stirred for 15 minutes and alkalized with concentrated ammonium hydroxide. Extraction was carried out with ethyl acetate and the extracts were washed with water, dried and evaporated to dryness. The residue was chromatographed on silica (eluant: hexane - ethyl acetate (9-1)) to obtain 0.57 g of the desired product melting at 70° C.

| IR Spectrum (CHCl₃): | |
|---|---|
| C-OCH₃ | 1718 cm⁻¹ |
| | 1437 cm⁻¹ |
| Aromatic | 1610 cm⁻¹ |
| + | 1574 cm⁻¹ |
| Heterocycle | 1554 cm⁻¹ |
| | 1499 cm⁻¹ |

EXAMPLE 10

4-[(3-butyl-1-ethylthio-4-isoquinolinyl)-methyl] benzoic acid

Using the procedure of Example 2, 500 mg of the product of Example 9 were reacted to obtain 490 mg of the desired product melting at 150° C. Crystallization from 30 ml of acetonitrile yielded 270 mg of product melting 171° C.

Analysis:
C₂₃H₂₅NO₂S; molecular weight = 379.53
| Calculated: | % C 72.78 | % H 6.64 | % N 3.69 | % S 8.44 |
|---|---|---|---|---|
| Found: | 72.6 | 6.7 | 3.9 | 8.5 |

| IR Spectrum (CHCl₃): | |
|---|---|
| C=O | 1692 cm⁻¹ |
| C=C | 1610 cm⁻¹ |
| + | 1574 cm⁻¹ |
| Aromatics | 1554 cm⁻¹ 1499 cm⁻¹ |

EXAMPLE 11

Methyl 4-[(3-butyl-4-isoquinolinyl)-methyl benzoate 5 g of Raney Nickel (washed beforehand in methanol) were added to a solution of 1.1 g of methyl 4-[[(3-butyl-1-ethylthio)-4-iso-quinolinyl]-methyl]-benzoate of Example 9 in 50 ml of methanol and the mixture was refluxed for 2 hours. The catalyst was filtered off and the mixture was washed with methanol. The filtrate was evaporated to dryness and the residue was chromatographed on silica (eluant: hexane - ethyl acetate (8-2)) to obtain 680 mg of the desired product.

| IR Spectrum | |
|---|---|
| C=O | 1718 cm⁻¹ |
| C=C | 1623 cm⁻¹ |
| + | 1611 cm⁻¹ |
| Aromatics | 1579 cm⁻¹ |
| | 1505 cm⁻¹ |
| | 1495 cm⁻¹ |
| CH₃ ester | 1437 cm⁻¹ |

EXAMPLE 12

4-[(3-butyl-4-isoquinolinyl)-methyl] benzoic acid

Using the procedure of Example 2, 680 mg of the product of Example 11 were reacted to obtain after crystallization from ethanol, 500 mg of the desired product melting at 212° C.

Analysis:
C₂₁H₂₁NO₂; molecular weight = 319.40
| Calculated: | % C 78.97 | % H 6.63 | % N 4.38 |
|---|---|---|---|
| Found: | 79.3 | 6.5 | 4.3 |

IR Spectrum (Nujol):
very associated absorption OH/NH region
C=C         1624-1612-1588-1580 cm⁻¹

EXAMPLE 13

Pharmaceutical composition

Tablets were prepared containing 10 mg of the product of Example 12 and sufficient excipient for a tablet of lactose, talc, starch and magnesium stearate weighing 100 mg.

Various modifications of the product and process of the invention may be made without departing from the spirit or scope thereof and it is to be understood that the invention is intended to be limited only as defined in the appended claims.

What we claim is:

1. A compound selected from the group consisting of a compound of the formula

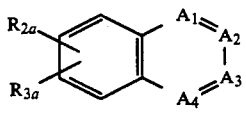

wherein one of $A_1$, $A_2$, $A_3$ and $A_4$ is nitrogen and the other three are

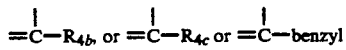

with the benzyl optionally substituted with a substituent selected from the group consisting of halogen, hydroxy, —CN, —CF₃, —NO₂, alkyl, alkenyl, alkoxy, alkylthio and acyl of an organic carboxylic acid of up to 6 carbon atoms, and free or alkyl of 1 to 4 carbon atoms esterified carboxy, $R_{2a}$ and $R_{3a}$ individually are selected from the group consisting of hydrogen, halogen, hydroxyl, mercapto, cyano, nitro, formyl, benzoyl, acyl of an organic carboxylic acid of up to 6 carbon atoms, alkyl, alkoxy and alkylthio of 1 to 6 carbon atoms, phenyl, naphthyl, benzyl, and phenylthio, all optionally substituted by one member of the group consisting of halogen, hydroxyl, alkoxy to 1 to 4 carbon atoms, trifluoromethyl, cyano, acyl of an organic carboxylic acid of up to 6 carbon atoms free, salified or alkyl of 1 to 4 carbon atoms esterified carboxy, tetrazolyl and isoxazolyl, amino, mono- or dialkyl of 1 to 4 carbon atoms amino, carbamoyl, pyrrolyl, pyrrolylmethyl, pyrrolylcarbonyl, $R_{4b}$ and $R_{4c}$ are individually selected from the group consisting of hydrogen, hydroxyl, cyano, carboxy free, salified and esterified by alkyl of 1 to 4 carbon atoms, alkyl, alkenyl, alkoxy, acyl of and organic carboxylic acid of up to 6 carbon atoms and alkylthio of up to 7 carbon atoms, all optionally substituted by one member of the group consisting of halogen, hydroxyl, nitro, alkyl, alkoxy and acyl of an organic carboxylic acid of up to 4 carbon atoms, trifluoromethyl, cyano or carboxy that is free, salified or esterified by alkyl of 1 to 4 carbon atoms, and their non-toxic, pharmaceutically acceptable acid addition salts.

2. A compound of claim 1 which is 4-[(3-butyly-4-quinolinyl)-methyl]-benzoic acid.

3. A composition for inhibiting the effects of angiotensin II comprising an effective amount of at least one compound of claim 1 sufficient to inhibit the effects of angiotensin II and an inert pharmaceutical carrier.

4. A method of inhibiting the effects of angiotensin II in warm-blooded animals comprising administering to warm-blooded animals an amount of a compound of claim 1 sufficient to inhibit angiotensin II effects.

* * * * *